(12) United States Patent
Hicks

(10) Patent No.: US 7,604,797 B2
(45) Date of Patent: Oct. 20, 2009

(54) COMPOSITIONS AND METHODS FOR TREATING BURNS

(75) Inventor: Terry Lee Hicks, Rego Park, NY (US)

(73) Assignee: BioMechanisms Inc., Rego Park, NY (US)

( * ) Notice: Subject to any disclaimer, the term of this patent is extended or adjusted under 35 U.S.C. 154(b) by 4 days.

(21) Appl. No.: 11/012,210

(22) Filed: Dec. 16, 2004

(65) Prior Publication Data

US 2005/0281820 A1 Dec. 22, 2005

Related U.S. Application Data

(63) Continuation of application No. PCT/US2004/031917, filed on Sep. 30, 2004.

(60) Provisional application No. 60/506,745, filed on Sep. 30, 2003.

(51) Int. Cl.
*A61K 31/74* (2006.01)

(52) U.S. Cl. .............. 424/78.06; 424/78.03; 424/78.05; 424/78.07; 514/886; 514/887

(58) Field of Classification Search ................ 424/1.11, 424/1.65, 9.1, 9.2, 78.03, 78.05, 78.06, 78.07; 514/886, 887, 889, 903
See application file for complete search history.

(56) References Cited

U.S. PATENT DOCUMENTS

| 4,132,572 A | * | 1/1979 | Parant et al. ................ 148/253 |
| 4,490,529 A | | 12/1984 | Rosowsky |
| 4,632,920 A | * | 12/1986 | Spillert et al. ................ 514/158 |
| 5,674,912 A | * | 10/1997 | Martin ........................ 514/724 |
| 5,863,938 A | | 1/1999 | Martin |
| 6,060,501 A | * | 5/2000 | Wachtel et al. ............... 514/423 |
| 6,093,743 A | * | 7/2000 | Lai et al. ..................... 514/599 |
| 2004/0014782 A1 | * | 1/2004 | Krause ........................ 514/313 |

OTHER PUBLICATIONS

Bronaugh et al (Journal of Investigative Dermatology, 1978, vol. 71, No. 4, pp. 263-265).*
Werner et al (Regional Anesthesia and Pain Medicine, 2002, vol. 27, No. 3, pp. 254-260).*
International Search Report for Application No. PCT/US04/31917; Dated: Apr. 25, 2005; International Searching Authority/USPTO.
Written Opinion of the international Searching Authority for Application N. PCT/US04/31917: Dated: Apr. 25, 2005; International Searching Authority/USPTO.

* cited by examiner

*Primary Examiner*—D L Jones
(74) *Attorney, Agent, or Firm*—The Law Offices of Andrew D. Fortney; Andrew D. Fortney; William K. Nelson

(57) ABSTRACT

The present invention provides compositions and methods for treating burns comprising administering to a burn area of a subject in need thereof of a therapeutically effective amount of a composition comprising an anti-cytokine or anti-inflammatory agent or a functional derivative thereof; and a pharmaceutically acceptable excipient.

43 Claims, 10 Drawing Sheets

Intact skin and underlying blood vessels are shown. White blood cells are circulating in the blood a concentration of about 4 million cells per milliliter of blood.

The acute burn injury causes immediate mechanical destruction of skin cells, generating an ulceration.

The acute burn injury generates immediate inflammation which results in production of the inflammatory cytokines tumor necrosis factor alpha (TNFα), Interleukin(IL)-1, IL-6, and IL-8. These cytokines originate from cells in the skin and cells in the deeper tissues.

Under the influence of IL-8 (a white blood cell attractant), white blood cells in the blood vessels are called into the tissues. The white cells dissolve tiny parts of the blood vessel walls in order to leave the circulation and infiltrate the tissues to arrive at the burn site. The white cells attempt to repair the damaged tissues and fight infection.

Under the influence of TNFα and IL-1, the cells that line the
blood vessels lose their integrity, and this results in pore
formation along the blood vessels. This results in leakage of
plasma from the blood vessels that causes edema fluid to
form in the surrounding tissues.

TNFα, IL-1, IL-6, and IL-8 are joined by other inflammatory substances, such as nitric oxide (NO) and free radicals (also called reactive oxygen intermediates or ROI). One important effect of these substances is dilation of the blood vessels that causes low blood pressure, and this can result in reduced blood pressure and even shock.

TNFα, IL-1, IL-6, and IL-8, and the other inflammatory substances, nitric oxide (NO) and free radicals or reactive oxygen intermediates (ROI) can gain access to the bloodstream and cause systemic inflammation.

Once TNFα, IL-1, IL-6, IL-8, nitric oxide (NO) and free radicals (ROI) enter the bloodstream, they can cause systemic inflammation. This can damage any organ system in the body, including the organs listed above. This also results in fever.

HR341g is thought to block production of the pro-inflammatory molecules TNFα, IL-1, IL-6, and IL-8 that initiate the inflammatory process. This not only reduces the local systemic damage that these molecules can cause, but it also blocks the formation of secondary inflammatory molecules like NO and ROI.

COMPOSITIONS AND METHODS FOR TREATING BURNS

CROSS REFERENCE TO RELATED APPLICATIONS

This application is a continuation of PCT/US2004/031917 application entitled. COMPOSITIONS AND METHODS FOR TREATING BURNS, filed Sep. 30, 2004, which claims priority to provisional U.S. application No. 60/506,745, filed Sep. 30, 2003, the disclosures of which are hereby incorporated in their entirety by reference.

FIELD OF THE INVENTION

This invention relates generally to beneficial effects obtained via administration of a pharmaceutical composition for the treatment of burns and skin wounds in warm-blooded animals, such as mammals and especially humans. In particular, the present invention is concerned with inflammation-associated tissue damage and is particularly directed to prophylactic and therapeutic methods for treating localized and systemic inflammation associated with burns, as well as the treatment of a variety of diseases associated with the inflammation that ensues from a burn.

BACKGROUND OF THE INVENTION

Burns

Burns are among the oldest, most complex and painful injuries known. Dating to antiquity, humans have been battling the devastating effects of burns. Burns are the second leading cause of accidental death in the United States, with post burn care being traumatic, painful, lengthy and emotionally draining for the patient. In fact, it has been estimated that over five million people are involved in burn accidents in the United States each year. Approximately 150,000 of these patients are hospitalized and over 6000 of these die each year (1).

Thermal burns are by far the most common types of burns. Although the skin is usually the part of the body that is burned, the tissues under the skin can also be burned, and internal organs can be burned even when the skin is not. For example, drinking a very hot liquid or caustic substance such as acid can burn the esophagus and stomach. Inhaling smoke or hot air from a fire in a burning building can burn the lungs. Tissues that are burned may die. When tissues are damaged by a burn, fluid may leak from blood vessels (capilliary permeability), causing swelling or edema. In an extensive burn, loss of a large amount of fluid from abnormally leaky blood vessels can cause shock. In shock, blood pressure decreases so much that too little blood flows to the brain and other vital organs.

Electrical burns may be caused by a temperature of more than 9,000° F., generated by an electric current when it passes from the electrical source to the body; this type of burn, sometimes called an electrical arc burn, usually completely destroys and chars the skin at the current's point of entry into the body. Because the resistance (the body's ability to stop or slow the current's flow) is high where the skin touches the current's source, much of the electrical energy is converted into heat there, burning the surface. Most electrical burns also severely damage the tissues under the skin. These burns vary in size and depth and may affect an area much larger than that indicated by the area of injured skin. Large electrical shocks can paralyze breathing and disturb heart rhythm, causing dangerously irregular heartbeats.

Chemical burns can be caused by various irritants and poisons, including strong acids and alkalis, phenols and cresols (organic solvents), mustard gas, and phosphorus. Chemical burns can cause tissue death that can slowly spread for hours after the burn.

Radiation burns can be caused by nuclear weapons, nuclear accidents, laboratory exposure, accidents during X-ray radiation chemotherapy, and over-exposure to sun. Radiation burns can cause inflammation, edema, ulcerations, damage to underlying endothelium and other cell types, as well as mutagenesis resulting in cancer, especially hematologic malignancies.

After suffering a burn injury, the affected individual can have usually has severe protein, muscle, and fat wasting in the area of the burn (1). Indeed, loss of up to 20% of body protein may occur in the first two weeks following a third degree or deep tissue burn injury (2). Increased oxygen consumption, metabolic rate, urinary nitrogen excretion, fat breakdown and steady erosion of body mass are all directly related to burn size. A return to normal levels as the burn wound heals gradually restores chemical balance, temperature and pH. To date no one has produced a treatment capable of preventing the life threatening inflammatory response a burn victim can endure.

Edema In General

Edema is the term generally used to describe the accumulation of excess fluid in the intercellular (interstitial) tissue spaces or body cavities. Edema may occur as a localized phenomenon such as the swelling of a leg when the venous outflow is obstructed; or it may be systemic as in congestive heart failure or renal failure. When edema is severe and generalized, there is diffuse swelling of all tissues and organs in the body and particularly pronounced areas are given their own individual names. For example, collection of edema in the peritoneal cavity is known as "ascites"; accumulations of fluid in the pleural cavity are termed plueral effusions; and edema of the pericardial sac is termed "pericardial effusion" or "hydropericardium". Non-inflammatory edema fluid such as accumulates in heart failure and renal disease is protein poor and referred to as a "transudate". In contrast, inflammatory edema related to increased endothelial permeability is protein rich and is caused by the escape of plasma proteins (principally albumin) and polymorphonuclear leukocytes (hereinafter "PMNs") to form an exudate.

Edema, whether inflammatory or non-inflammatory in nature, is thus an abnormality in the fluid balance within the microcirculation which includes the small arterioles, capillaries, and post-capillary venules of the circulatory system. Normal fluid balance and exchange is critically dependent on the presence of an intact and metabolically active endothelium. Normal endothelium is a thin, squamous epithelium adapted to permit selective, rapid exchange of water and small molecules between plasma and interstitium; but one which limits the passage of many plasma proteins.

A variety of different disturbances can induce a condition of edema. These include: an elevated venous hydrostatic pressure which may be caused by thrombosis of a vein or any other venous obstruction, heart failure; hypoproteinemia with reduced plasma oncotic pressure resulting from either inadequate synthesis or increased loss of albumin; increased osmotic pressure of the interstitial fluid due to abnormal accumulation of sodium in the body because renal excretion of sodium cannot keep pace with the intake; failure of the lymphatics to remove fluid and protein adequately from the interstitial space; an increased capillary permeabiity to fluids and proteins as occurs in the inflammatory response to tissue injury; and an increased mucopolysaccharide content within the interstitial spaces.

Currently accepted therapeutic treatments for edema include those biogenic and synthetic pharmacological agents used to treat generalized inflammations, of which edema is just one clinical manifestation. Such agents are said to inhibit the synthesis of pro-inflammatory molecules; and can include such agents as aspirin, ibuprofen (salicylates and propionate derivatives), steroids, and anti-histamines. These agents have a wide scale of effectiveness and, in general, are most valuable in the treatment of minor inflammatory problems that produce only minor, localized edemas. There are few, if any, agents that are therapeutically effective in the treatment of severe, local and systemic edemas. Furthermore, as far as is known, there is no effective agent in present use as a prophylactic against these conditions. Also, albumin infusion and congestive heart failure medications are useful in treatment of edema when used appropriately.

Current Treatments for Thermally Induced Burns

Current treatments for thermally induced burns include the use of topical agents and various surgical procedures. The topical agents that are used to treat burns are limited. Representative examples of such topical agents include, without limitation, Bacitracin, Polymyxin B Sulfate, Neomycin, Polysporin/Neosporin, Povidone, Silver Sulfadiazine, *Nitrofura* sp, Gentamicin, Manfenide Acetate, Nystatin, Sodium Hypochlorite Solution, Silver Nitrate, TAB Solution, and Chlorhexadine Solution. However, none of these drugs stops edema.

Due to the unacceptable rate and risk of infections from using only topical treatments (without the removal of the burned tissues), procedures called escharotomy and debridement were introduced. Escharotomy literally means cutting a hole in the eschar, the thick, rigid barrier of burn tissue. It is an emergency treatment for any full thickness, and almost invariably, circumferential burn to the dermis. It is relevant particularly to the neck, thorax and extremities. Burned skin is called eschar. Debridement is the removal of eschar tissue. Skin grafts are layers of skin, which are taken from a suitable donor area of a patient and transplanted to a recipient area of damaged skin. Using debridement alone, the rate of infection is still extremely high but with the use of skin grafts the infection rate is lowered. Pig skin and/or allografts may be used instead of the patients own skin. Debridement and skin grafts in their present form, however, do not completely restore the function of healthy skin. The transplanted skin lacks oil glands, sweat glands, hair follicles, and have no nerve endings at the injury site(s). Furthermore, the grafted skin is prone to deformities such as hypertrophic scarring. Currently it takes many months or even years to complete these extremely painful procedures.

In view of the above, there is continuing need in the art to develop better compositions and methods for treating the inflammation with edema that is associated with all forms of burns. The methods and compositions of the present invention provide for the first time a reproducible means for ameliorating and/or treating the negative effects associated with burns by blocking one or more of components of the inflammatory pathway. The inventors have satisfied these and other long felt needs with the following invention.

SUMMARY OF THE INVENTION

The present invention provides a method for treating burns comprising administering to a burn area of a subject in need thereof a therapeutically effective amount of a composition comprising an anti-cytokine or anti-inflammatory agent or a functional derivative thereof; and a pharmaceutically acceptable excipient.

The present invention provides a method for treating burns comprising administering to a burn area of a subject in need thereof a therapeutically effective amount of a composition comprising HR341g or a functional derivative thereof; and a pharmaceutically acceptable excipient.

In one aspect, the present invention relates to methods of controlling or alleviating pain by reducing the severity of inflammation and edema associated with a burn comprising administering to a subject in need thereof a therapeutically effective amount of a pharmaceutical composition comprising an anti-cytokine or anti-inflammatory agent or a functional derivative thereof; and a pharmaceutically acceptable excipient, wherein said pharmaceutical composition inhibits one or more components of the inflammatory pathway.

In one aspect, the present invention relates to methods of controlling or alleviating pain by reducing the severity of pulmonary edema associated with a burn comprising administering to a subject in need thereof a therapeutically effective amount of a pharmaceutical composition comprising an anti-cytokine or anti-inflammatory agent or a functional derivative thereof; and a pharmaceutically acceptable excipient, wherein said pharmaceutical composition inhibits one or more components of the inflammatory pathway.

The present invention relates to methods of controlling or alleviating pain by reducing the severity of inflammation and edema associated with a burn comprising administering to a subject in need thereof a therapeutically effective amount of a pharmaceutical composition comprising HR341g or a functional derivative thereof; and a pharmaceutically acceptable excipient, wherein said pharmaceutical composition inhibits one or more components of the inflammatory pathway.

The present invention also relates to a method for promoting rapid healing and/or regeneration of damaged tissues resulting from a burn comprising administering to a subject in need thereof a therapeutically effective amount of a pharmaceutical composition comprising an anti-cytokine or anti-inflammatory agent or a functional derivative thereof; and a pharmaceutically acceptable excipient, wherein said pharmaceutical composition promotes rapid healing and/or regeneration of damaged tissues while retaining the original composition of the tissue and minimizing complications and scarring associated with a burn.

The present invention also relates to a method for promoting rapid healing and/or regeneration of damaged tissues resulting from a burn comprising administering to a subject in need thereof a therapeutically effective amount of a pharmaceutical composition comprising HR341g or a functional derivative thereof; and a pharmaceutically acceptable excipient, wherein said pharmaceutical composition promotes rapid healing and/or regeneration of damaged tissues while retaining the original composition of the tissue and minimizing complications and scarring associated with a burn.

In another aspect, the present invention also relates to a method for preventing or ameliorating the adverse affects associated with controlled thermal induced skin damage employed in scar and tattoo removal, cancer excisions, cautery excision of polyps, ulcers, treatment of decubitus ulcers (bedsores), acne, cutaneous fungal infections comprising administering to a subject in need thereof a therapeutically effective amount of a pharmaceutical composition comprising an anti-cytokine or anti-inflammatory agent or a functional derivative thereof; and a pharmaceutically acceptable excipient, wherein said pharmaceutical composition promotes rapid regeneration of damaged tissues while retaining the original composition of the tissue and minimizing complications and scarring associated with the thermally induced burn in one or more of the recited conditions.

The present invention relates to methods of preventing or ameliorating blistering or pain associated with overexposure to sun comprising administering to a subject in need thereof a therapeutically effective amount of a pharmaceutical composition comprising an anti-cytokine or anti-inflammatory agent or a functional derivative thereof; and a pharmaceutically acceptable excipient.

In yet another aspect, the present invention relates to a method for preventing or ameliorating the deleterious inflammatory response and/or the adverse sequellae associated with controlled therapeutic thermal induced skin damage employed in the use of lasers for the treatment of medical conditions and the use of induced thermal injury in various cosmetic procedures comprising administering to a subject in need thereof a therapeutically effective amount of a pharmaceutical composition comprising an anti-cytokine or anti-inflammatory agent or a functional derivative thereof; and a pharmaceutically acceptable excipient, wherein said pharmaceutical composition prevents or ameliorates the deleterious inflammatory response and/or the adverse sequellae associated with such controlled therapeutic thermal induced skin damage.

In another aspect of the present invention, a method is provided for the use of pharmaceutical compositions comprising HR341g or a functional derivative thereof to diminish pain or inflammation comprising blocking one or more components of the inflammatory pathway.

In another aspect of the present invention, a method is provided for the use of a synthetic drug comprising an anti-cytokine or anti-inflammatory agent or functional derivative thereof to diminish pain or inflammation associated with a burn comprising blocking one or more components of the inflammatory pathway.

In certain specific embodiments, each of the above-recited methods are accomplished by the administration to a subject in need thereof of a therapeutically effective amount of one or more antagonists or inhibitors to one or more enzymes or components of the inflammatory pathway wherein administration of the enzyme antagonist or inhibitor is sufficient to block one or more components of the inflammatory pathway. While not intended to be limited to any particular mechanism of action, the specific enzymes or components of the inflammatory pathway which may be inhibited using each of the aforementioned methods of the present invention include, inter alia, dihydrofolate reductase, enolase, Interleukin-1 beta converting enzyme (ICE), tumor necrosis factor alpha converting enzyme (TACE), nitric oxide synthase, thromboxane synthase, cyclooxygenase, denylate cyclase, histone deacetylase, elastase, proteinase 3, thrombin, or any combination thereof.

In one specific embodiment, each of the above-recited methods are accomplished by the administration to a subject in need thereof of a therapeutically effective amount of one or more antagonists to the enzyme dihydrofolate reductase sufficient to block one or more components of the inflammatory pathway. In one embodiment, the therapeutically effective amount of one or more antagonists to the enzyme dihydrofolate reductase is sufficient to block one or more components of the glycolytic pathway.

In another specific embodiment, each of the above-recited methods are accomplished by the administration to a subject in need thereof of a therapeutically effective amount of one or more antagonists to the enzyme enolase sufficient to block one or more components of the inflammatory pathway. In one embodiment, the therapeutically effective amount of one or more antagonists to the enzyme enolase is sufficient to block one or more components of the glycolytic pathway.

For each of the above-recited methods of the present invention, the therapeutically effective amount of one or more an anti-cytokine or anti-inflammatory agents, one or more antagonists to the enzyme dihydrofolate reductase, and/or one or more antagonists to the enzyme enolase may be administered to a subject in need thereof in conjunction with a therapeutically effective amount of one or more anti-inflammatory compounds and/or a therapeutically effective amount of one or more immunomodulatory agents.

In certain embodiments of the method of the present invention, the anti-inflammatory compound or immunomodulatory drug comprises interferon; interferon derivatives comprising betaseron, .beta.-interferon; prostane derivatives comprising iloprost, cicaprost; glucocorticoids comprising cortisol, prednisolone, methyl-prednisolone, dexamethasone; immunsuppressives comprising cyclosporine A, methoxsalene, sulfasalazine, azathioprine, methotrexate; lipoxygenase inhibitors comprising zileutone, MK-886, WY-50295, SC-45662, SC-41661A, BI-L-357; leukotriene antagonists; peptide derivatives comprising ACTH and analogs thereof; soluble TNF-receptors; anti-TNF-antibodies; soluble receptors of interleukins or other cytokines; antibodies against receptors of interleukins or other cytokines, T-cell-proteins; and calcipotriols and analogues thereof taken either alone or in combination.

In yet another aspect of the invention, a method is provided for suppressing or modulating the immune system in a mammalian patient in need of such immunosuppression comprising administering to said patient an immunosuppressing effective amount of a therapeutically effective amount of a pharmaceutical composition comprising an anti-cytokine or anti-inflammatory agent or a functional derivative thereof; and a pharmaceutically acceptable excipient.

In yet another aspect of the invention, a method is provided for suppressing or modulating the immune system in a mammalian patient in need of such immunosuppression comprising administering to said patient an immunosuppressing effective amount of a therapeutically effective amount of a pharmaceutical composition comprising HR341g or a functional derivative thereof; and a pharmaceutically acceptable excipient.

In yet another aspect of the invention, a method is provided for suppressing the synthesis of potentially harmful inflammatory molecules comprising cytokines (for example, IL-1, IL-2, IL-8, IL-12, IL-18, TNF), nitric oxide, reactive oxygen intermediates (ROI), leukotrenes, and/or prostaglandins, or any one or more of the known biological molecules involved in inflammatory signal transduction pathways, etc. in a mammalian patient in need of such immunosuppression comprising administering to said patient an immunosuppressing effective amount of a pharmaceutical composition comprising an anti-cytokine or anti-inflammatory agent or a functional derivative thereof; and a pharmaceutically acceptable excipient, wherein said pharmaceutical composition suppresses the synthesis of cytokines, or any one or more of the known biological molecules involved in the activation of inflammatory signal transduction pathways leading to a blockade of inflammation or reduced immune response, or a combination thereof.

In yet another aspect of the invention, a method is provided for suppressing the synthesis of potentially harmful inflammatory molecules comprising cytokines (for example, IL-1, IL-2, IL-6, IL-8, IL-12, IL-18, TNF), nitric oxide, reactive oxygen intermediates (ROD, leukotrenes, and/or prostaglandins, or any one or more of the known biological molecules involved in inflammatory signal transduction pathways, etc. in a mammalian patient in need of such immunosuppression comprising administering to said patient an immunosuppressing effective amount of a pharmaceutical composition comprising HR341g or a functional derivative thereof; and a pharmaceutically acceptable excipient, wherein said pharmaceutical composition suppresses the synthesis of cytokines, or any one or more of the known biological molecules involved in the activation of inflammatory signal transduction pathways leading to a blockade of inflammation or reduced immune response, or a combination thereof.

In yet another aspect of the invention, a method is provided for ameliorating the diseases associated with inflammatory mediators and the systemic response to a burn injury. The initial burn or inflammation and edema involves oxidant and arachidonic acid metabolites, which trigger neutrophils and macrophages to release cytokines, including, but not limited to, tumor necrosis factor, IL-1, IL-2, IL-8, IL-12, IL-18, as well as nitric oxide. Endotoxins from pathogens in the wound and/or the gastrointestinal tract initiate and enhance inflammation and can result in the translocation of microorganisms across the gut and generate pathology at distant sites which would otherwise be unaffected by the trauma. The exaggerated response is called the "two hit" hypothesis, but "afterburn" is more descriptive. The post-burn septic response is caused by excessive inflammatory mediators derived from the host, especially IL-1, IL-2, TNF, IL-8, NO, reactive oxygen intermediates (ROI), and its complications. These complications or "associated disease responses" (ADRs) are caused by edema, inflammation, and the translocation of microbial flora. Since an anti-cytokine or anti-inflammatory agents such as, but not limited to HR341g and functional derivatives thereof inhibit the edema and inflammatory response, anti-cytokine or anti-inflammatory agents such as, but not limited to HR341g and functional derivatives thereof have the ability to treat diseases where inflammation contributes to the disease process.

A list of the typical ADRs includes, but is not limited to, those that are post-burn complications such as compartment syndrome, acidosis, acute renal failure, acute tubular necrosis, cellulitis, secondary seizures, contractures, reduced end-organ perfusion, endotoxemia, exotoxemia, gangrene, nosocomial pneumonia (50% of patients with burn/smoke inhalation injury develop this type), ARDS (acute respiratory distress syndrome), ventilator associated pneumonia, sepsis, septic shock, cachexia, diarrhea, encephalopathy, myglobulinuria, smoke inhalation-induced lung injury, thromboembolic complications, and those other non-burn associated diseases with an inflammatory component such as, but not limited to, anemia, cancer, congestive heart failure, coagulated blood vessels (thrombosis), dermatomyositis (DM), dermatitis, alveolar proteinosis pneumonia, bronchcolotis obliterans organizing pneumonia (BOOP), chronic aspiration lipoid pneumonia, community acquired pneumonia (CAP), coronavirus pneumonia, cryptoccal pneumonia, chlamydia pneumonia, desquamative interstitial pneumonia, eosinophilic pneumonia, *haemophilus influenza* pneumonia, *haemophilus parainfluenzae* pneumonia, idiopathic pneumonia, influenza associated pneumonia, idiopathic interstitial pneumonia, *kliebsiella* pneumonia, *mycoplasma* pneumonia, non-specific interstitial pneumonia (associated with dermatomyositis-DM), *pasteurella multocida* pneumonia, *pneumocystis carinii*-(PCP) pneumonia, *pseudomonas aeruginosa* pneumonia, respiratory synctial virus infection, staphylococcal necrotising pneumonia, tuberculosis pneumonia, usual interstitial pneumonitis (UIP), varicella zoster virus pneumonia, toxic shock syndrome, and toxic epidermal necrosis (TEN). The following list of diseases are associated with metabolic disarray because of thermal injuries: cachexia, diarrhea, encephalopathy, myglobulinuria, and neurities.

In yet another aspect of the invention, a method is provided for modulating expression of major histocompatibility complex molecules in a mammalian patient in need of such inflammatory-suppression comprising administering to said patient an inflammatory-suppression effective amount of a therapeutically effective composition comprising HR341g or a functional derivative thereof; and a pharmaceutically acceptable excipient, wherein said pharmaceutical composition modulates expression of major histocompatibility complex molecules.

In another embodiment, the pharmaceutical compositions of the present invention are thus useful to treat the pain associated with and/or prevent a disease or disorder often accompanying a burn wherein said disease or disorder is selected from the group consisting of: myocardial ischemia, tissue and muscle-associated ischemia, extremity-associated ischemia, stroke, sepsis, amyotrophic lateral sclerosis (ALS), seizures, extension of strokes after initial tissue damage, functional brain damage secondary to primary and secondary brain tumors, local brain damage secondary to meningitis or brain abscess, viral meningitis, viral encephalitis, and/or local brain damage secondary to trauma, transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes mellitus, juvenile-onset or recent-onset diabetes mellitus, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, Lichen planus, Pemphigus, bullous pemphigoid, Epidermolysis bullosa, urticaria, angioedemas, vasculitis, erythema, cutaneous eosinophilia, Lupus erythematosus, acne, Alopecia areata, keratoconjunctivitis, vernal conjunctivitis, uveitis associated with Behcet's disease, keratitis, herpetic keratitis, dystrophia epithelialis corneae, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, Celrac diseases, proctitis, eosinophilic gastroenteritis, mastocytosis, Crohn's disease, ulcerative colitis, rhinitis, eczema, interstitial nephritis, Goodpasture's syndrome, hemolytic-uremic syndrome, diabetic nephropathy, myositis, Guillain-Barre syndrome, polyneuritis, mononeuritis, radiculopathy, pure red cell aplasia, aplastic anemia, hypoplastic anemia, idiopathic thrombocytopenic purpura, autoimmune hemolytic anemia, pernicious anemia, megaloblastic anemia, osteoporosis, sarcoidosis, fibroid lung, idiopathic interstitial pneumonia, dermatomyositis, photoallergic sensitivity, cutaneous T cell lymphoma, atherosclerosis, aortitis syndrome, polyarteritis nodosa, myocardosis, scleroderma, Wegener's granulomatosis, Sjogren's syndrome, eosinophilic fascitis, lesions of gingiva, male pattern alopecia or alopecia senilis by preventing epilation or providing hair germination and/or promoting hair generation and hair growth, Sezary's syndrome, Addison's disease, ischemia-reperfusion injury of organs, endotoxin-shock, pseudomembranous colitis, colitis caused by drug or radiation, ischemic acute renal insufficiency, chronic renal insufficiency, lung cancer, pulmonary emphysema, dermatitis erythema multiforme, linear IgA ballous dermatitis, carcinogenesis, metastasis of carcinoma, Behcet's disease, autoimmune hepatitis, primary biliary cirrhosis, sclerosing cholangitis, partial liver resection, acute liver necrosis, necrosis caused by toxin, viral hepatitis, shock, or anoxia, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, cancer, trauma, and chronic bacterial infection.

In one aspect of the invention, the therapeutically effective amount of the one or more anti-cytokine or anti-inflammatory agents administered to a subject in need thereof is that amount sufficient to reduce or inhibit, inter alia, the pathology associated with one or more of the following diseases: myocardial ischemia, tissue and muscle-associated ischemia, extremity-associated ischemia, stroke, sepsis, amyotrophic lateral sclerosis (ALS), seizures, extension of strokes after initial tissue damage, functional brain damage secondary to primary and secondary brain tumors, local brain damage secondary to meningitis or brain abscess, viral meningitis, viral encephalitis, and/or local brain damage secondary to trauma, transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes mellitus, juvenile-onset or recent-onset diabetes mellitus, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, Lichen planus, Pemphigus, bullous pemphigoid, Epidermolysis bullosa, urticaria, angioedemas, vasculitis, erythema, cutaneous eosinophilia, Lupus erythematosus, acne, Alopecia areata, keratoconjunctivitis, vernal conjunctivitis, uveitis associated with Behcet's disease, keratitis, herpetic keratitis, dystrophia epithelialis corneae, ocular pemphigus, Mooren's ulcer, Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, Celrac diseases, proctitis, eosinophilic gastroenteritis, mastocytosis, Crohn's disease, ulcerative colitis, rhinitis, eczema, interstitial nephritis, Goodpasture's syndrome, hemolytic-uremic syndrome, diabetic nephropathy, myositis, Guillain-Barre syndrome, polyneuritis, mononeuritis, radiculopathy, pure red cell aplasia, aplastic anemia, hypoplastic anemia, idiopathic thrombocytopenic purpura, autoimmune hemolytic anemia, pernicious anemia, megaloblastic anemia, osteoporosis, sarcoidosis, fibroid lung, idiopathic interstitial pneumonia, dermatomyositis, photoallergic sensitivity, cutaneous T cell lymphoma, atherosclerosis, aortitis syndrome, polyarteritis nodosa, myocardosis, scleroderma, Wegener's granulomatosis, Sjogren's syndrome, eosinophilic fascitis, lesions of gingiva, male pattern alopecia or alopecia senilis by preventing epilation or providing hair germination and/or promoting hair generation and hair growth, Sezary's syndrome, Addison's disease, ischemia-reperfusion injury of organs, endotoxin-shock, pseudomembranous colitis, colitis caused by drug or radiation, ischemic acute renal insufficiency, chronic renal insufficiency, lung cancer, pulmonary emphysema, dermatitis erythema multiforme, linear IgA ballous dermatitis, carcinogenesis, metastasis of carcinoma, Behcet's disease, autoimmune hepatitis, primary biliary cirrhosis, sclerosing cholangitis, partial liver resection, acute liver necrosis, necrosis caused by toxin, viral hepatitis, shock, or anoxia, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, cancer, trauma, and chronic bacterial infection.

In one embodiment, the reduction or inhibition of pathology and/or symptoms associated with one or more of each of the above-recited indications is on the order of about 10-20% reduction or inhibition. In another embodiment, the reduction or inhibition of pathology and/or symptoms is on the order of 30-40%. In another embodiment, the reduction or inhibition of pathology and/or symptoms is on the order of 50-60%. In yet another embodiment, the reduction or inhibition of the pathology and/or symptoms associated with each of the recited indications is on the order of 75-100%. It is intended herein that the ranges recited also include all those specific percentage amounts between the recited range. For example, the range of about 75 to 100% also encompasses 76 to 99%, 77 to 98%, etc, without actually reciting each specific range therewith.

In yet another aspect, the present invention is directed to a method of relieving or ameliorating the pathology or symptoms associated with any one or more of the above-identified diseases or indications in a mammal suffering from any one or more of the above-identified diseases or indications which comprises administering to the mammal in need thereof a therapeutically effective pathology or symptom-reducing amount of a pharmaceutical composition comprising one or more anti-cytokine or anti-inflammatory agents, either alone or in combination with one or more anti-inflammatory compounds or immunomodulatory agents; and a pharmaceutically acceptable carrier or excipient, wherein said anti-cytokine or anti-inflammatory agent is sufficient to inhibit one or more components of the inflammatory pathway.

The present invention also relates to the use of the HR341g pharmaceutical composition in combination with one or more antibacterial or antiviral compositions or any combination thereof for treating any one of the aforementioned diseases, or any combination thereof.

The present invention provides methods for therapeutically or prophylactically treating edema in a subject.

The method for therapeutically treating edema comprises the step of administering an effective amount of an anti-cytokine or anti-inflammatory agent or derivative thereof to the subject after occurrence of the edema.

The method for prophylactically treating edema comprises the step of administering an effective amount of an anti-cytokine or anti-inflammatory agent or derivative thereof to the subject prior to the occurrence of edema.

Either methodology inhibits the permeability of the microvasculature fluid, macromolecules, and blood cells thereby acting directly on the clinical edema and reducing the activation of detrimental metabolic cascades and pathways that require activation of the inflammatory pathway.

In one aspect of the invention, the pharmaceutical compositions of the present invention are administered orally, systemically, via an implant, intravenously, topically, intrathecally, or nasally.

In one aspect of the invention, the pharmaceutical compositions of the present invention are administered to the burn area within 5, 10, 20, 30, 40, 50, and 60 minutes of the event causing the burn. Preferably, the pharmaceutical compositions of the present invention are administered to the burn area within 10 to 20 minutes of the event causing the burn. Most preferably, the pharmaceutical compositions of the present invention are administered to the burn area as soon as possible following the event causing the burn. The pharmaceutical compositions of the present invention should be administered to the burn area as soon as possible but may also be administered up to twelve hours following the burn event.

In one embodiment of the invention, the burn being treated is a thermally induced burn, a thermally induced controlled burn, a chemical burn, a radiation burn, an electrical burn, an ice burn, or a burn caused by exposure to lightening.

In each of the above described methods, the burns are either first, second, third or fourth degree burns or any combination thereof.

In certain embodiments of the methods of the present invention, the subject or mammal is a human.

In other embodiments of the methods of the present invention, the subject or mammal is a veterinary and/or a domesticated mammal.

In yet another aspect, the present invention provides a kit for use in emergency burn accidents or injuries for application of the pharmaceutical composition for immediate application to the skin as soon after the accidental burn or burn injury as possible.

In another aspect, the present invention provides a topical burn treatment formulation suitable for use in fire extinguishers that may be used to cover individuals whose bodies and/or clothes are engulfed in flames, wherein said formulation comprises an anti-cytokine, an anti-inflammatory agent, or HR341g or a functional derivative thereof.

There has been thus outlined, rather broadly, the important features of the invention in order that a detailed description thereof that follows can be better understood, and in order that the present contribution can be better appreciated. There are additional features of the invention that will be described hereinafter.

In this respect, before explaining at least one embodiment of the invention in detail, it is to be understood that the invention is not limited in its application to the details as set forth in the following description and figures. The present invention is capable of other embodiments and of being practiced and carried out in various ways. Additionally, it is to be understood that the terminology and phraseology employed herein are for the purpose of description and should not be regarded as limiting.

As such, those skilled in the art will appreciate that the conception, upon which this disclosure is based, can readily be used as a basis for designing other methods for carrying out the several features and advantages of the present invention. It is important, therefore, that the claims be regarded as including such equivalent constructions insofar as they do not depart from the spirit and scope of the present invention.

DETAILED DESCRIPTION OF THE INVENTION

Figure 1A:
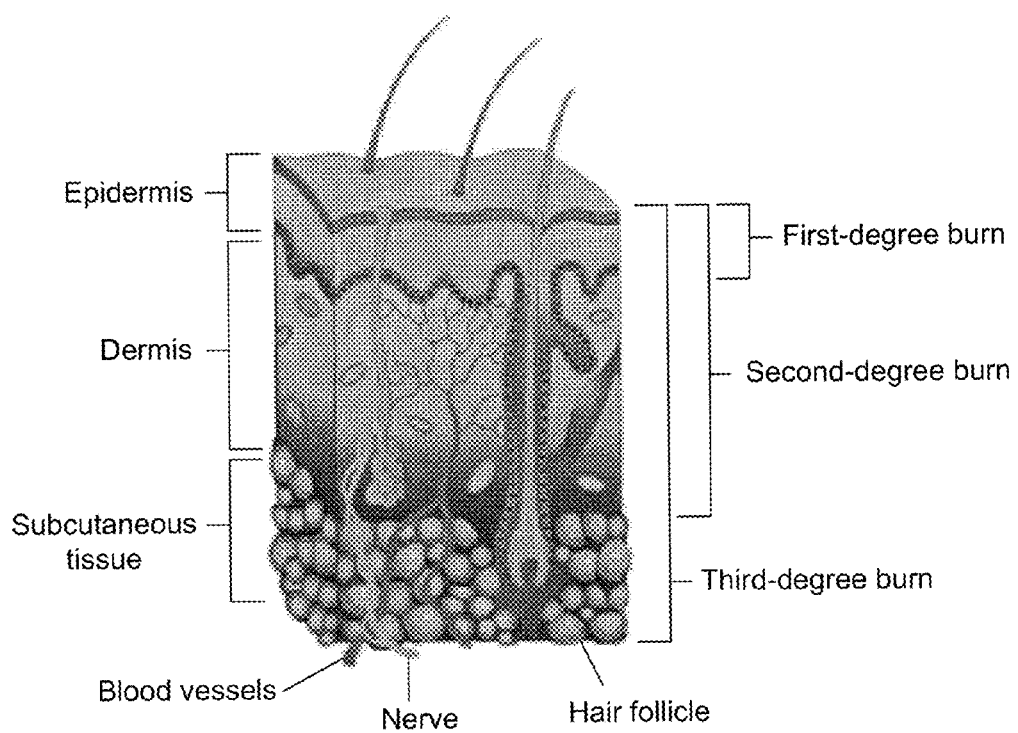
FIG. 1A-J illustrates the formation of edema following a burn injury and the effect of administration of HR341g on inflammatory cytokines such as cytokines tumor necrosis factor alpha (TNFa), IL-1, IL-6, and IL-8, and other inflammatory molecules such as NO and ROI.
Figure 1B:
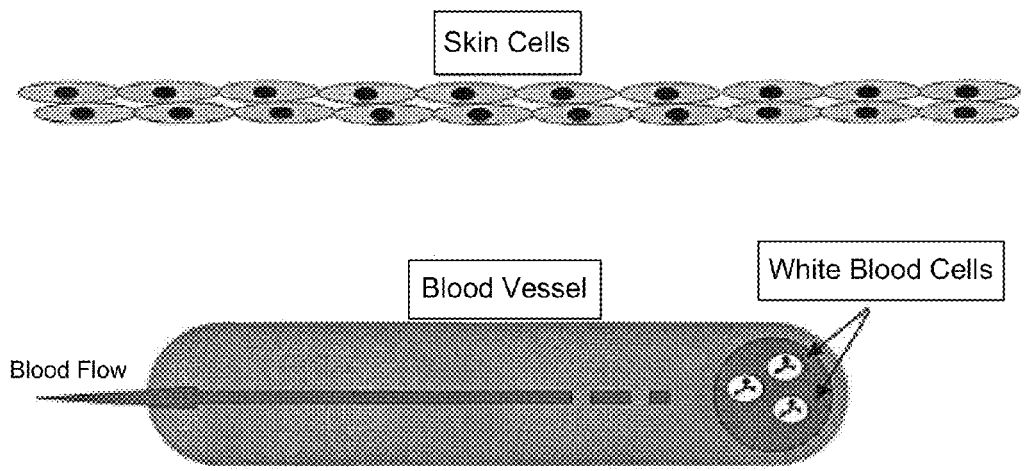
Figure 1C:
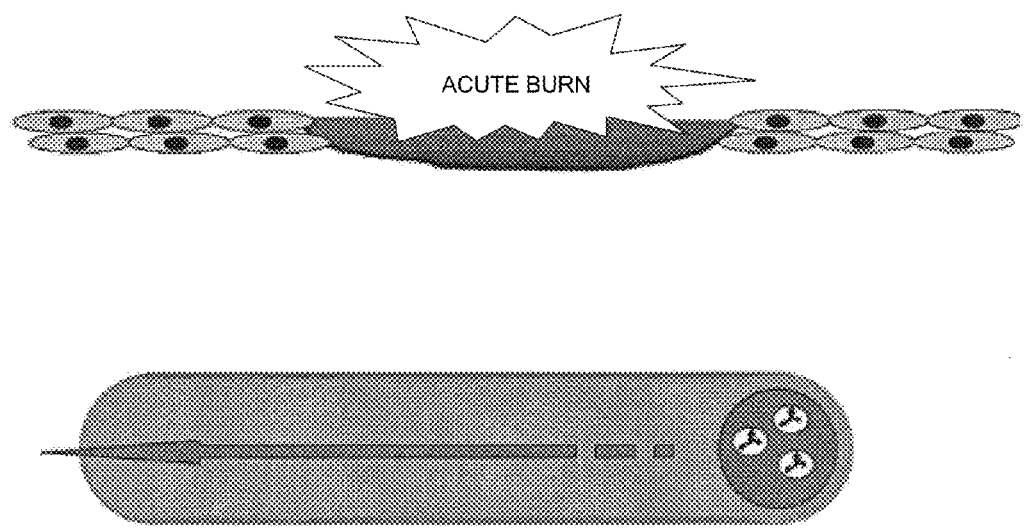
Figure 1D:
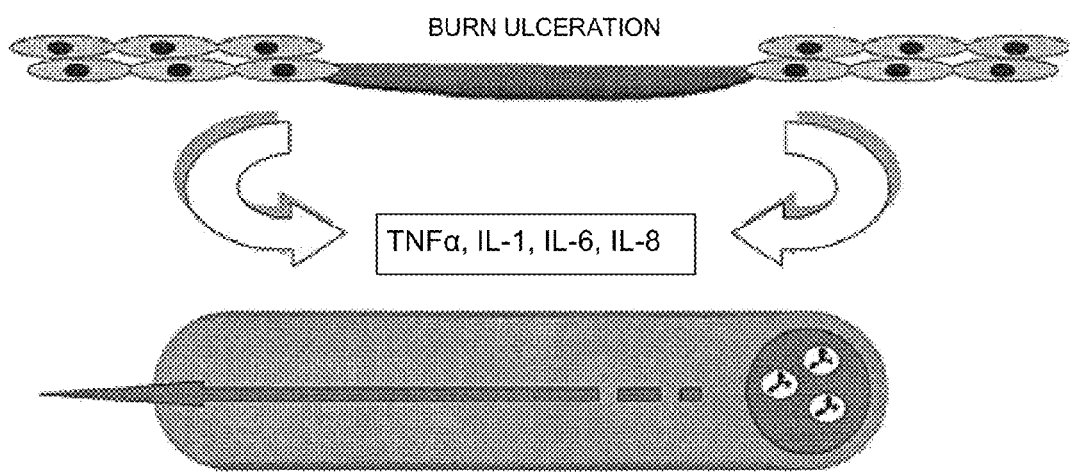
Figure 1E:
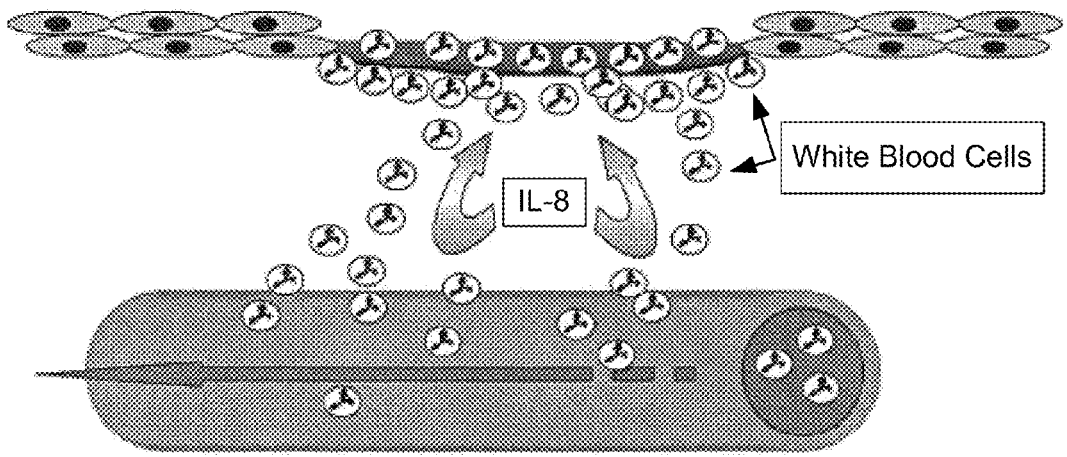
Figure 1F:
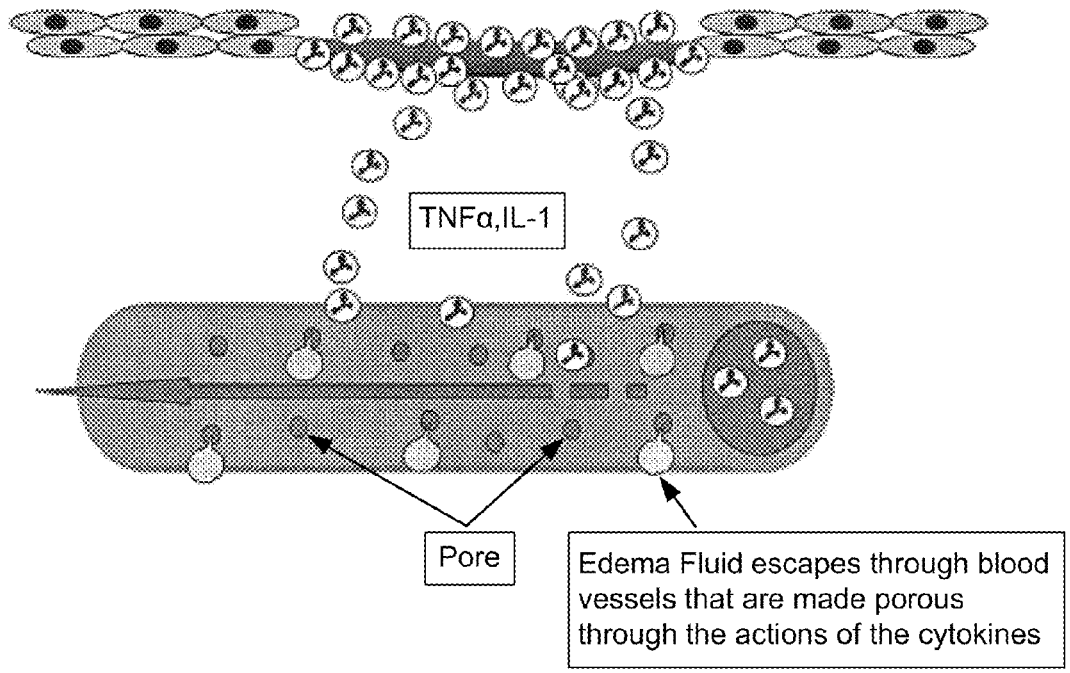
Figure 1G:
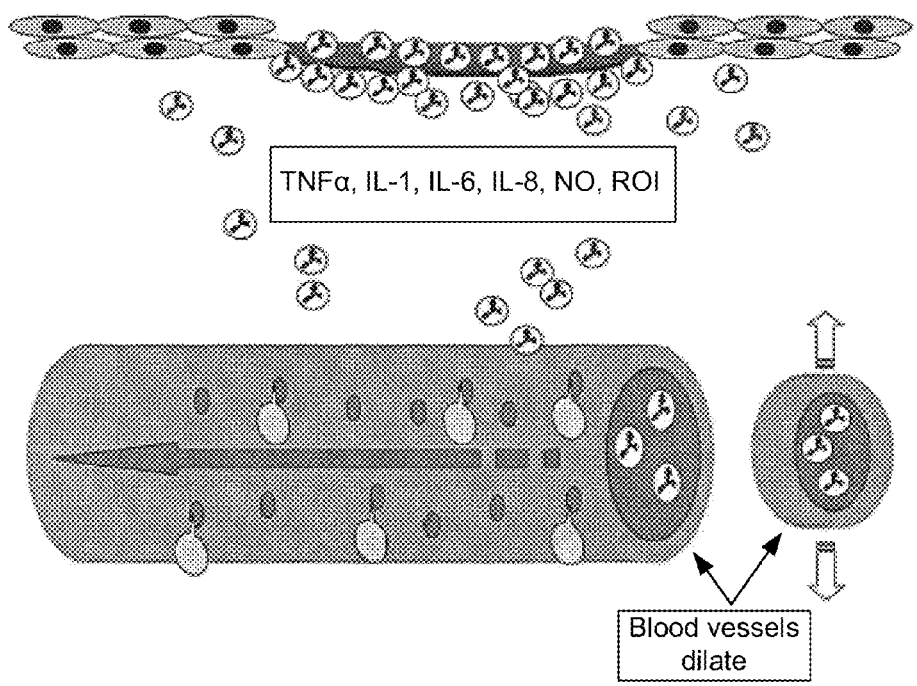
Figure 1H:
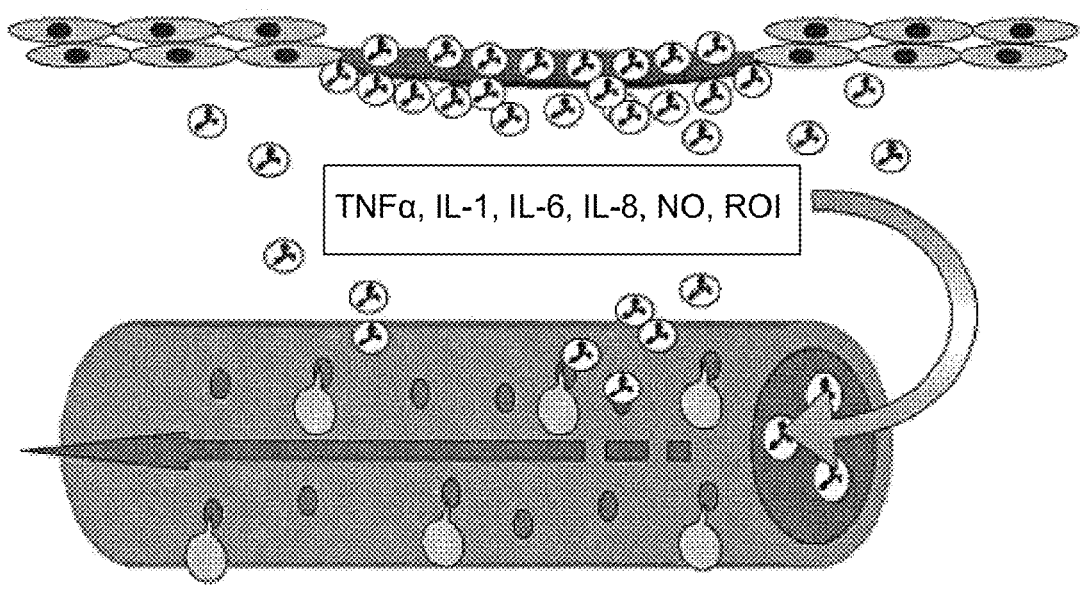
Figure 1I:
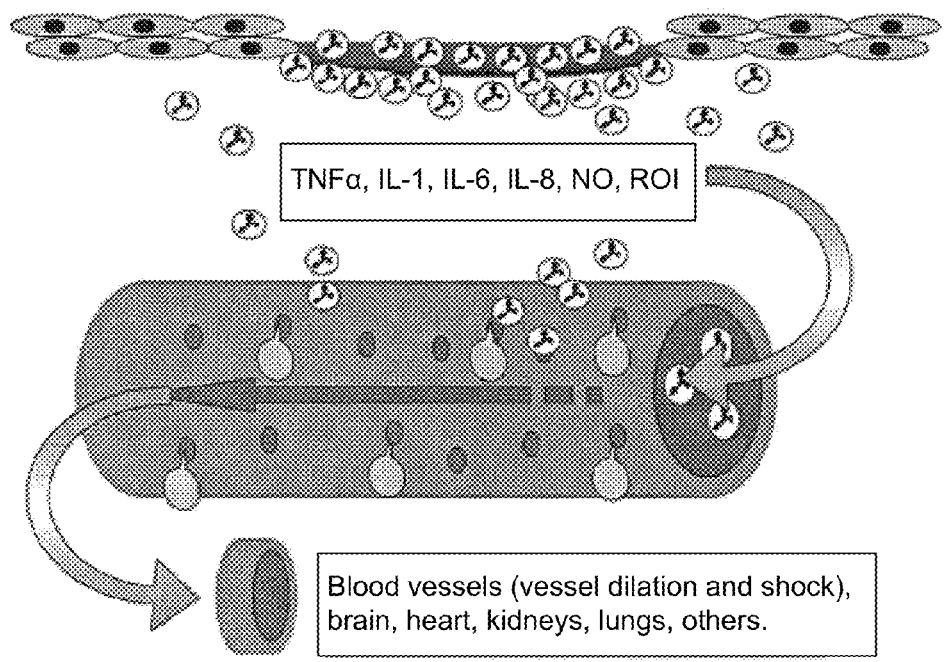
Figure 1J:
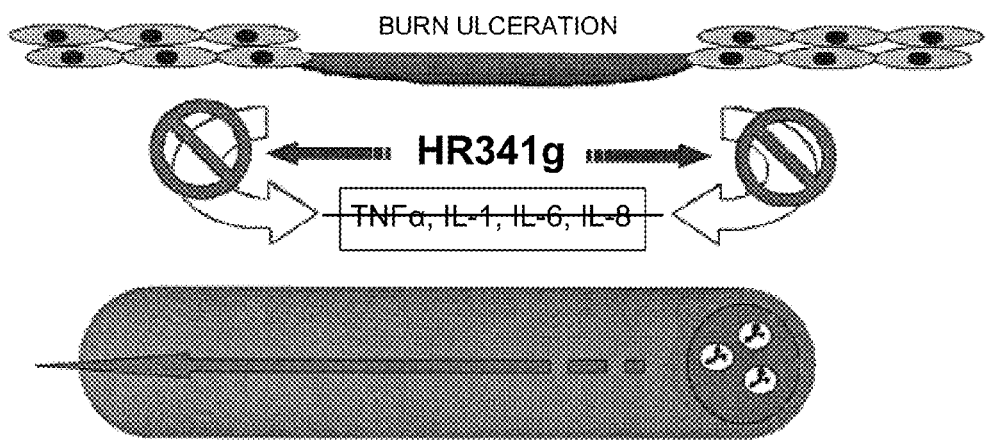

The present invention in its simplest form provides a composition and method for treating burns, edema and associated disease responses that accompany various types of burns. What follows is a brief description of the types of burns and associated edemas and other diseases that may be treated with the compositions and methods of the present invention.

Types of Burns

Superficial or 1st degree burns. The body will always develop edema after a burn, with sunburns and 1st degree burns not having visible blisters because a minimal amount of plasma is lost. Clinical signs include painful erythema. Histologically, the epidermis is partially destroyed and the basal membrane remains intact. Usually the prognosis for a first degree burn is that it heals in a few days.

Partial Thickness or 2nd degree burns. These burns will almost always blister as will some 3rd degree burn injuries. Clinical signs include erythema, blisters, underlying tissue blanches with pressure. Histologically, the basal membrane is partially destroyed. Usually the prognosis for a partial thickness or 2nd degree burn is that it heals in ten to fifteen days.

Deep 2nd degree burns. Clinical signs include erythyema, blisters, and that the underlying tissue does not blanche with pressure. Histologically, the basal membrane is entirely destroyed; the dermis is partially destroyed, epidermal cells are still present around hair follicles. Usually the prognosis for a deep 2nd degree burn is that it heals in three to four weeks, or does not heal and therefore may require grafting.

Full Thickness or 3rd degree burns. These are not as likely to blister because the skin is usually destroyed. Clinical signs include brown, black or white; no blister, no sensitivity. Histologically, the epidermis and dermis is totally destroyed; subcutaneous tissues are more or less injured. Usually the prognosis for a full thickness or 3rd degree burn is that it does not heal except from the edges and therefore requires grafting.

Fourth degree burns. These burns can involve the destruction of underlying muscle and tendons. Clinical signs include blackened appearance, dryness, severe pain. Histologically, the skin, underlying tissue, muscles, tendons, and bones, are destroyed. Usually the prognosis for a fourth degree burn is that it does not heal and therefore requires debridement and grafting.

Edema

Edema is found in all types of burns, including, for example, those caused by heat, extreme cold, radiation, chemicals and electricity. It related to pain, infection, debridement, skin grafts, amputation, scarring, shock and death. If true success at treating a burn is to be achieved, it is going to be during the pre-edema window of opportunity. Edema usually begins to form 30 minutes to two (2) hours after receiving the burn with peak formation occurring at 48 hrs. A thirty minute to 2 hour window gives ample time to treat the patient with the compositions and methods of the present invention.

Thus, by preventing and/or treating inflammation in all types of burns, it is possible to reduce edema formation. The compositions and methods of the present invention trigger the proper healing sequence required in all forms of burns and therefore prevents the destructive biochemical reactions typically brought on by a burn.

Moreover, by preventing and/or treating edema, it is also possible to modulate the "after-burn" sequence of events so that the burn is prevented from becoming deeper and wider. The compositions and methods of the present invention are able to effectively reduce after-burn by blocking ongoing inflammation. After the composition of the present invention has been applied to a burn, it prevents tissue damage that would otherwise occur. The composition of the present invention adheres to the walls of the epitheal lining and the lining of the hair follicles, thereby protecting each in the after-burn period. The compositions of the present invention will also prevent microorganisms from invading the burn site. Patients will therefore also suffer less because they remain free from various infections commonly associated with typical burns. The composition thus prevents burn injuries from progressing to greater severity.

By preventing and/or treating inflammation, it is possible to inhibit the complex chemical changes, which often become the determining factors in a patient's outcome. The composition of the present invention curtails these chemical changes making the body react the way it would after lesser traumas such as a mild wound or cut instead of a burn. After a mild cut or wound, the body begins to clog the wound with platelets so the healing stage can begin. This is a normal response that promotes repair of the injured area.

With the compositions and methods of the present invention it is also possible to prevent and/or treat infections caused by bacteria, as well as being able to prevent and/or treat numerous Associated Disease Responses (ADR's). The use of compositions and methods of the present invention prevents the tissue damage that is the breeding ground for microorganisms in most burns. This reduced rate of infection translates to reduced disease, disorders and deformities. The ability to interfere with the cycle of infection in sequellae can halt the disease process. Gram-positive and gram-negative organism infections usually develop after edema. The destructive consequences of these pathophysiological phases are related to MOD (Multiple Organ Dysfunction) at an early stage. The translocation of microorganisms can be prevented if the area of plasma leakage can be blocked. The compositions of the present invention prevent the accumulation of neutrophils, and their release of oxygen free radicals and various proteases by limiting inflammation, thereby prohibiting further tissue damage.

A list of the typical ADRs includes, but is not limited to, those which are burn-associated such as compartment syndrome, acidosis, acute renal failure, acute tubular necrosis, cellulitis, secondary seizures, contractures, reduced end-organ perfusion, endotoxemia, exotoxemia, gangrene, nosocomial pneumonia (50% of patients with burn/smoke inhalation injury develop this type), ARDS (acute respiratory distress syndrome), ventilator associated pneumonia, sepsis, septic shock, thromboembolic complications, and those other non-burn associated diseases with an inflammatory component such as, but not limited to, anemia, cancer, congestive heart failure, reduced end-organ perfusion, dermatomyositis (DM), dermatitis, alveolar proteinosis pneumonia, bronchcolotis obliterans organizing pneumonia (BOOP), chronic aspiration lipid pneumonia, community acquired pneumonia (CAP), coronavirus pneumonia, cryptoccal pneumonia, chlamydia pneumonia, desquamative interstitial pneumonia, eosinophilic pneumonia, *haemophilus influenza* pneumonia, *haemophilus influenza* pneumonia, *haemophilus parainfluenzae* pneumonia, idiopathic pneumonia, influenza associated pneumonia, idiopathic interstitial pneumonia, *kliebsiella* pneumonia, *mycoplasma* pneumonia, non-specific interstitial pneumonia (associated with dermatomyositis-DM), *pasteurella multocida* pneumonia, *pneumocystis carinnii*-(PCP) pneumonia, *pseudomonas aeruginosa* pneumonia, respiratory synctial virus infection, staphylococcal necrotising pneumonia, tuberculosis pneumonia, usual interstitial pneumonitis (UIP), varicella zoster virus pneumonia, toxic shock syndrome, and toxic epidermal necrosis (TEN). The following list of diseases are associated with metabolic disarray because of thermal injuries: cachexia, diarrhea, encephalopathy, myglobulinuria, and neurities.

It is also possible to prevent the usual debridement and requirement for skin grafting often necessary for third degree or higher burns. By using the composition of the present invention, patients will suffer less pain and trauma associated with burn injuries. Patients will develop reduced edema and burns will heal naturally, reducing the necessity for the more invasive treatment of debridement and skin grafting. Skin grafting can be complicated by infection and can leave unsightly and disfiguring scars. In serious burns that require debridement, the opportunity to grow an individual's own skin may be lost making long and painful skin graft procedures necessary. In some cases, amputation is the only solution. Many full thickness burns can now be healed using the composition of the present invention with reduced need for debridement and/or skin grafting.

By preventing inflammation, it is also possible to prevent hypertrophic scarring that typically occurs with more serious burns. Burns from partial superficial to full thickness can be healed without infection or hypertrophic scarring if inflammation and tissue damage is reduced. With full thickness or 3rd degree burns, there is no dermis, so collagen fibers are not aligned vertically and horizontally, but are present in random, disordered masses. The proliferation phase begins, yet progress is difficult. During remodeling, the collagen fibers are supposed to be tightly aligned but because of infections, debridement, skin grafts and other disorders, the process is not organized. This dysfunction can lead to hypertrophic scarring. If there is reduced inflammation/infection present, there is a reduced requirement to remove the patient's remaining skin, and so the body can repair itself with fewer complications and with little to no scarring. The compositions and methods of the present invention allow the body to elicit the proper repair sequence.

HR341g Composition and Derivatives Thereof

Representative examples of naturally occurring and non-naturally generated anti-cytokine or anti-inflammatory agents or functional derivatives thereof that may be used in the prophylactic and therapeutic methods for treating localized and systemic inflammation associated with burns include, for example, but not limited to, pharmaceutical compositions comprising HR341g, aminopterin, methotrexate, pyramethamine, and trimethoprim or any combination thereof.

Aminopterin (AMT; 4-amino-4-deoxy-pteroylglutamic acid) is a dihydofolate reductase inhibitor. Dihydrofolate reductase (DHFR) catalyzes the reaction of 7,8-dihydrofolate and NADPH to form 5,6,7,8,-tetrahydofolate and $NADP^+$. Tetrahydofolate is essential for the biosynthesis of purines, thymidylate and several amino acids (Rajagopalan et al. PNAS vol. 99 (21), 13481-13486 (2002), incorporated by reference herein). Aminopterin acts as an antineoplastic agent by interfering with one or more biosynthetic steps involving folate coenzymes of the cell. The structural formula of aminopterin is as follows:

Structure of Aminopterin

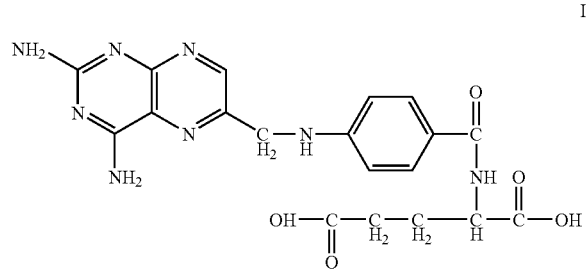

I

Methotrexate (MTX; 4-amino-4-deoxy-N.sup.10-methyl-pteroylglutamic acid) and Aminopterin (AMT; 4-amino-4- deoxy-pteroylglutamic acid) are dihydrofolate reductase inhibitors ( ) and act as antineoplastic agents by interfering with one or more biosynthetic steps involving folate coenzymes of the cells. The structure of MTX differs from AMT in that the former contains a methyl group in the N.sup.10 position while the latter does not, having hydrogen instead. The structural formula of MTX is as follows:

Structure of MTX

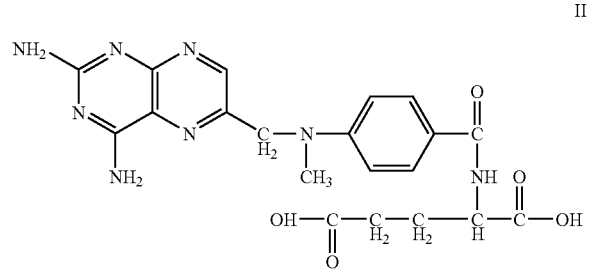

The following references describe the preparation of methotrexate [see Seeger et al., J. Am. Chem. Soc., 1949, 71:1753]; the metabolism of methotrexate [see Freeman, J. Pharmacol. Exp. Ther. 1958, 122:154; and Henderson et al., Cancer Res. 1965, 25:1008, 1018]; the toxicity of methotrexate [Condit et al., Cancer 1960, 13:222-249]; the pharmacokinetic models of methotrexate [Bischoff, et al., J. Pharm. Sci 1970, 59:149]; the metabolism and pharmacokinetics of methotrexate [Evans, Appl. Pharmacokinet. 1980, 518-548]; the clinical pharmacology of methotrexate [Bertino, Cancer Chemother, 1981, 3: 359-375; Jolivet et al., N. Engl. J. Med., 1983, 309: 1094-1104—the texts of each of which references are expressly incorporated by reference herein].

MTX and AMT have been found to be effective clinically against certain malignant tumors: for example, good to excellent tumor response has been seen in patients with acute lymphocytic leukemia, Burkitt's lymphoma, carcinoma of the breast, mycosis fungoides, epidermoid cancer of the head and neck area, and osteogenic sarcoma. In addition, MTX is the drug of choice in the treatment of choriocarcinoma and is also used for certain non-neoplastic conditions such as generalized psoriasis and certain autoimmune diseases such as rheumatoid arthritis and lupus erythematosus.

However, it should be noted that chemotherapy with MTX or AMT is accompanied by a variety of toxicities, partly related to their ability to form polyglutamates, which limit the effectiveness of the compounds and their long-term use.

It will be recognized and appreciated that Formulas I and II are presented herein using conventional chemical structure, format, and notations for amino acids and peptide organization as those found in Albert L. Lehninger's text, Biochemistry, The Molecular Basis Of Cell Structure And Function, 2nd edition, Worth Publishers, Inc., 1977—the text of which is expressly incorporated by reference herein. Moreover, Formulas I and II by their definitions intend that all presently known and future embodiments of naturally occurring and non-naturally generated substances—which are by chemical formulation and structure members forming the class of compounds of dihydrofolate reductase inhibitors or dihydrofolate reductase inhibitor functional derivatives thereof (including all substituted and derivatized forms)—lie within the scope of the present invention. However, representative, non-limiting, examples of embodiments are those formulated and synthesized as described by U.S. Pat. Nos. 5,965,106, 5,140,104, and 4,956,461—the texts of each of which are being expressly incorporated by reference herein. These issued patents not only provide representative embodiments of naturally occurring and non-naturally generated dihydrofolate reductase inhibitors or dihydrofolate reductase inhibitor functional derivatives thereof; but also provide complete and detailed procedures and techniques for synthesizing and purifying such dihydrofolate reductase inhibitor functional analogues for use in the methodologies of the present invention.

Additionally, pyramethamine, and trimethoprim are, by chemical formulation and structure, intended to be part of the members forming the class of compounds of dihydrofolate reductase inhibitors or dihydrofolate reductase inhibitor functional derivatives thereof. Thus pyramethamine, and trimethoprim and all substituted and derivatized forms of pyramethamine, and trimethoprim are also intended to be encompassed within the scope of methodologies of the present invention.

The dihydrofolate reductase inhibitor compounds or functional derivatives thereof for use in the methods of the present invention may be prepared by the reaction of 4-amino-4-deoxy-pteroic acid or 4-amino-4-deoxy-N.sup.10-methylpteroic acid with cysteic or homocysteic acid. Thus, representative examples of compounds for use in the methods of the present invention comprise, without limitation, those MTX derivative compounds such as: 4-amino-4-deoxy-N.sup.10-methylpteroyl-D,L-homocysteic acid (mAPA-D,L-HCysA), 4-amino-4-deoxy-N.sup.10-methylpteroyl-L-cysteic acid (mAPA-L-CysA), 4-amino-4-deoxy-N.sup.10-methylpteroyl-L-homocysteic acid (mAPA-L-HCysA), 4-amino-4-deoxypteroyl-D,L-homocysteic acid (APA-D,L-HCysA), 4-amino-4-deoxypteroyl-L-cysteic acid (APA-L-CysA), and 4-amino-4-deoxypteroyl-L-homocysteic acid (APA-L-HCysA).

For example, and not by way of limitation, the compounds for use in the methods of the present invention comprise MTX and AMT analogues in which the glutamic acid moiety of MTX or AMT is replaced by cysteic acid or homocysteic acid.

Additional non-limiting examples of aminopterin derivatives that may be used in the methods of the present invention are provided as follows: alpha-carboxyl substituted aminopterin derivatives—for example, in one embodiment of aminopterin derivatives, alpha-carboxyl-substituted aminopterin derivatives including alpha-carboxylester derivatives, alpha-carboxylamide derivatives, alpha-carboxylpeptide derivatives, and alpha-carboxylhydrazide derivatives may be used; alpha-carboxylamide derivatives—non-limiting examples of which include alpha-carboxylester derivatives of aminopterin include the alpha-methylester, alpha-ethylester, alpha-propylester, alpha-butylester, alpha-pentylester, alpha-hexylester, alpha-heptylester and alpha-octylester of aminopterin, in which the esters may be formed from the n- or iso-form of the corresponding alcohols—Further examples include other ester derivatives such as the alpha-benzylester of aminopterin; alpha-carboxylamide derivatives—non-limiting examples of which include the alpha-amide, alpha-butylamide, alpha-benzylamide, and the alpha-amidoethane sulfonic acid derivative of aminopterin; alpha-carboxylpeptide derivatives—non-limiting examples of which include the alpha-glycyl derivative, alpha-aspartyl derivative, alpha-glutamyl derivative and the alpha-polyglutamyl [1-5] derivative of aminopterin; alpha-carboxylhydrazide derivatives—non-limiting examples of which include the alpha-carboxylhydrazide derivative of aminopterin; gamma-carboxyl substituted aminopterin derivatives—In one embodiment of aminopterin derivatives, gamma-carboxylsubstituted aminopterin derivatives including gamma-carboxylester derivatives, gamma-carboxylamide derivatives, gamma-carboxylpeptide derivatives, and gamma-carboxylhydrazide derivatives may be used; gamma-carboxylester derivatives—non-limiting examples of which include gamma-carboxylester derivatives include the gamma-methylester, gamma-ethylester, gamma-propylester, gamma-butylester, gamma-pentylester, gamma-hexylester, gamma-heptylester; and the gamma-octylester of aminopterin, of which the esters may be synthesized from the n- or iso-form of the corresponding alcohols—Further examples include other ester derivatives such as the gamma-benzylester derivative of aminopterin; gamma-carboxylamide derivatives—non-limiting examples of which include the gamma-amide, gamma-butylamide, gamma-benzylamide, and the gamma-amidoethane sulfonic acid derivative of aminopterin; gamma-carboxylpeptide derivatives—non-limiting examples of which include the gamma-glycyl derivative, gamma-aspartyl derivative, gamma-glutamyl derivative, and the gamma-polyglutamyl [1-5] derivative of aminopterin; gamma-carboxylhydrazide derivatives—non-limiting examples of which include the gamma-carboxylhydrazide derivative of aminopterin; alpha, gamma-homobisubstituted aminopterin derivatives—One embodiment of aminopterin derivatives comprise alpha, gamma-homobisubstituted aminopterin derivatives including alpha, gamma-dicarboxylester derivatives, alpha, gamma-dicarboxylamidederivatives, alpha, gamma-dicarboxylpeptide derivatives, and alpha, gamma-dicarboxylhydrazide derivatives may be used; alpha, gamma-dicarboxylester derivatives—non-limiting examples of which include the alpha, gamma-dimethylester, alpha, gamma-diethylester, alpha, gamma-dipropylester, alpha, gamma-dibutyl ester, alpha, gamma-dipentyl ester alpha, gamma-dihexylester, alpha, gamma-diheptylester, and the alpha, gamma-dioctylester of aminopterin, the esters of which may be synthesized from the n- or iso-form of the corresponding alcohols. Further examples include other diester derivatives such as the alpha, gamma-dibenzylester derivative of aminopterin; alpha, gamma-dicarboxylamide derivatives—non-limiting examples of which include the alpha, gamma-diamide, alpha, gamma-dibenzylamide, and the alpha, gamma-diamidomethane sulfonic acid derivative of aminopterin.; alpha, gamma-dicarboxylpeptide derivatives—non-limiting examples of which include the alpha, gamma-diglycyl, alpha, gamma-diaspartyl, alpha, gamma-diglutamyl, and the alpha, gamma-dipolyglutamyl [1-5] derivative of aminopterin.; alpha, gamma-dicarboxylhydrazide derivatives—non-limiting examples of which include the alpha, gamma-dicarboxylhydrazide derivatives of aminopterin; alpha, gamma-heterobisubstituted aminopterin derivatives—One embodiment of aminopterin derivatives comprise alpha, gammaheterobisubstituted aminopterin derivatives including alpha, gamma-dicarboxylester derivatives, alpha-ester, gamma-amide derivatives, and alpha-ester, gamma-hydrazide derivatives; alpha, gamma-dicarboxylester derivatives—non-limiting examples of which include the alpha-methylester, gamma-butylester of aminopterin and the alpha-methylester, gamma-benzylester of aminopterin; alpha-ester, gamma-amide derivatives—non-limiting examples of which include the alpha-benzylester, gamma-butylamide derivative; alpha-benzylester, gamma-benzylamide derivative; alpha-benzylester, gamma-butylamide-p-toluene sulfonic acid derivative; and the alpha-benzylester, gamma-benzylamide-p-toluene sulfonic acid derivative of aminopterin; alpha-Ester, gamma-hydrazide derivatives—non-limiting examples of which include the alpha-t-butylester, gamma-hydrazide derivative of aminopterin; other alpha, gamma-heterobisubstituted derivatives—non-limiting examples of include the alpha, gamma-diamide derivatives; alpha, gamma-dipeptide derivatives; alpha, gamma-dihydrazide derivatives; alpha-ester, gamma-amide derivatives; alpha-ester, gamma-peptide derivatives; alpha-amide, gamma-ester derivatives; alpha-amide, gamma-peptide derivatives; alpha-amide, gamma-hydrazide derivatives; alpha-peptide, gamma-ester derivatives; alpha-peptide, gamma-ester derivatives; alpha-peptide, gamma-amide derivatives; alpha-peptide, gamma-hydrazide derivatives; alpha-hydrazide, gamma-ester derivatives; alpha-hydrazide, gamma-amide derivatives; and the alpha-hydrazide, gamma-peptide derivatives of aminopterin.

Additional non-limiting examples of MTX derivatives that may be used in the methods of the present invention are provided as follows: alpha-carboxyl substituted MTX derivatives—for example, in one embodiment of MTX derivatives, alpha-carboxyl-substituted MTX derivatives including alpha-carboxylester derivatives, alpha-carboxylamide derivatives, alpha-carboxylpeptide derivatives, and alpha-carboxylhydrazide derivatives may be used; alpha-carboxylamide derivatives—non-limiting examples of which include alpha-carboxylester derivatives of MTX include the alpha-methyl ester, alpha-ethylester, alpha-propylester, alpha-butylester, alpha-pentylester, alpha-hexylester, alpha-heptylester and alpha-octylester of MTX, in which the esters may be formed from the n- or iso-form of the corresponding alcohols—Further examples include other ester derivatives such as the alpha-benzylester of MTX; alpha-carboxylamide derivatives—non-limiting examples of which include the alpha-amide, alpha-butylamide, alpha-benzylamide, and the alpha-amidoethane sulfonic acid derivative of MTX; alpha-carboxylpeptide derivatives—non-limiting examples of which include the alpha-glycyl derivative, alpha-aspartyl derivative, alpha-glutamyl derivative and the alpha-polyglutamyl [1-5] derivative of MTX; alpha-carboxylhydrazide derivatives—non-limiting examples of which include the alpha-carboxylhydrazide derivative of MTX; gamma-carboxyl substituted MTX derivatives—In one embodiment of MTX derivatives, gamma-carboxyl-substituted MTX derivatives including gamma-carboxylester derivatives, gamma-carboxylamide derivatives, gamma-carboxylpeptide derivatives, and gamma-carboxylhydrazide derivatives may be used; gamma-carboxylester derivatives—non-limiting examples of which include gamma-carboxylester derivatives include the gamma-methylester, gamma-ethylester, gamma-propylester, gamma-butylester, gamma-pentylester, gamma-hexylester, gamma-heptylester; and the gamma-octylester of MTX, of which the esters may be synthesized from the n- or iso-form of the corresponding alcohols—Further examples include other ester derivatives such as the gamma-benzylester derivative of MTX; gamma-carboxylamide derivatives—non-limiting examples of which include the gamma-amide, gamma-butylamide, gamma-benzylamide, and the gamma-amidoethane sulfonic acid derivative of MTX; gamma-carboxylpeptide derivatives—non-limiting examples of which include the gamma-glycyl derivative, gamma-aspartyl derivative, gamma-glutamyl derivative, and the gamma-polyglutamyl [1-5] derivative of MTX; gamma-carboxylhydrazide derivatives—non-limiting examples of which include the gamma-carboxylhydrazide derivative of MTX; alpha, gamma-homobisubstituted MTX derivatives—One embodiment of MTX derivatives comprise alpha, gamma-homobisubstituted MTX derivatives including alpha, gamma-dicarboxylester derivatives, alpha, gamma-dicarboxylamide derivatives, alpha, gamma-dicarboxylpeptide derivatives, and alpha, gamma-dicarboxylhydrazide derivatives may be used; alpha, gamma-dicarboxylester derivatives—non-limiting examples of which include the alpha, gamma-dimethylester, alpha, gamma-diethylester, alpha, gamma-dipropylester, alpha, gamma-dibutylester, alpha, gamma-dipentylester alpha, gamma-dihexylester, alpha, gamma-diheptylester, and the alpha, gamma-dioctylester of MTX, the esters of which may be synthesized from the n- or iso-form of the corresponding alcohols. Further examples include other diester derivatives such as the alpha, gamma-dibenzylester derivative of MTX; alpha, gamma-dicarboxylamide derivatives—non-limiting examples of which include the alpha, gamma-diamide, alpha, gamma-dibenzylamide, and the alpha, gamma-diamidomethane sulfonic acid derivative of MTX.; alpha, gamma-dicarboxylpeptide derivatives—non-limiting examples of which include the alpha, gamma-diglycyl, alpha, gamma-diaspartyl, alpha, gamma-diglutamyl, and the alpha, gamma-dipolyglutamyl [1-5] derivative of MTX.; alpha, gamma-dicarboxylhydrazide derivatives—non-limiting examples of which include the alpha, gammadicarboxylhydrazide derivatives of MTX; alpha, gamma-heterobisubstituted MTX derivatives—One embodiment of MTX derivatives comprise alpha, gammaheterobisubstituted MTX derivatives including alpha, gamma-dicarboxylester derivatives, alpha-ester, gamma-amide derivatives, and alpha-ester, gamma-hydrazide derivatives; alpha, gamma-dicarboxylester derivatives—non-limiting examples of which include the alpha-methylester, gamma-butylester of MTX and the alpha-methylester, gamma-benzylester of MTX; alpha-ester, gamma-amide derivatives—non-limiting examples of which include the alpha-benzylester, gamma-butylamide derivative; alpha-benzylester, gamma-benzylamide derivative; alpha-benzylester, gamma-butylamide-p-toluene sulfonic acid derivative; and the alpha-benzylester, gamma-benzylamide-p-toluene sulfonic acid derivative of MTX; alpha-Ester, gamma-hydrazide derivatives—non-limiting examples of which include the alpha-t-butylester, gamma-hydrazide derivative of MTX; other alpha, gamma-heterobisubstituted derivatives—non-limiting examples of include the alpha, gamma-diamide derivatives; alpha, gamma-dipeptide derivatives; alpha, gamma-dihydrazide derivatives; alpha-ester, gamma-amide derivatives; alpha-ester, gamma-peptide derivatives; alpha-amide, gamma-ester derivatives; alpha-amide, gamma-peptide derivatives; alpha-amide, gamma-hydrazide derivatives; alpha-peptide, gamma-ester derivatives; alpha-peptide, gamma-ester derivatives; alpha-peptide, gamma-amide derivatives; alpha-peptide, gamma-hydrazide derivatives; alpha-hydrazide, gamma-ester derivatives; alpha-hydrazide, gamma-amide derivatives; and the alpha-hydrazide, gamma-peptide derivatives of MTX.

Other possible examples of folic acid analogues that may be used in the methods of this invention include: 3',5' Dichloromethotrexate, 3',5' Dichloroaminopterin, 5,8-Dideazamethotrexate, 5,8 Dideaza 5,6,7,8-tetrahydromethotrexate, 5,8-Dideaza 5,6,7,8-tetrahydroaminopterin, 5,8,10-Trideazaminopterin, 5,10-Dideazatetrahydrofolic acid, 8,10-Dideazaminopterin.

Also specifically contemplated for use within the methods of the invention are amine derivatives of the aforementioned and other folic acid analogs. Such amine derivatives encompass any folic acid analog containing or modified to contain a reactive amine moiety. The term "reactive amine" is intended to encompass any nitrogen-containing functional group that can be covalently attached or bonded through a nitrogen atom to an aldehyde functional group either by a single chemical condensation reaction or by a chemical condensation reaction followed by reduction to stabilize the covalent bond formed. Thus amine derivatives of folic acid analogs useful according to the invention include but are not limited to: methotrexate gammahydrazide, methotrexate-alpha-hydrazide, 3'5-dichloromethotrexate-gammahydrazide, 3',5-dichloromethotrexate-alpha-hydrazide, methotrexate-alpha-alpha-lysyl-glycyl-glycyl-tyrosyl hydrazide (SEQ ID NO: 1), methotrexate-gamma-tyrosyl hydrazide, methotrexate-alpha-lysyl hydrazide, methotrexate-alpha-alpha-lysine, methotrexate-alpha-alpha-lysyl-epsilon-arginine-glycine-glycine-tyrosine (SEQ ID NO: 2), aminopterin-gamma-hydrazide, aminopterin-alpha-hydrazide, 3'5'dichloraminopterin-gamma-hydrazide, 3'5'-dichloroaminopterin-alpha-hydrazide, aminopterin-gamma-tyrosyl hydrazide, aminopterin-alpha-alpha-lysyl-glycyl-tyrosyl hydrazide, aminopterin-alpha-alpha-lysyl hydrazide, aminopterin-alpha-alpha-lysine, and aminopterin-alpha-alpha-lysyl-epsilon-arginine-glycine-glycine-tyrosine (SEQ ID NO: 3). Reactive amine-containing derivatives of folic acid analogs such as 5,8dideazamethotrexate, 5,8-dideaza 5,6,7,8-tetrahydromethotrexate, 5,8,-dideaza 5,6,7,8-tetrahydroaminopterin, 5,8,10-trideazatetrahydrofolic acid, and 8,10-dideazaminopterin are also useful according to the methods of the present invention.

It is also specifically contemplated within the scope of the invention that the amine derivatives of the afore-mentioned folic acid analogs or derivatives thereof are particularly well suited for use in the preparation of therapeutic antibody conjugates, which therapeutic antibody conjugates may be used in the methods of the present invention to prevent edema associated with all types of burns. Thus, these derivatives represent intermediates in the preparation of therapeutic antibody-folic acid analog conjugates. Selective attachment of the folic acid analogs via a reactive amine to an oxidized carbohydrate moiety of an antibody or antibody fragment results in a conjugate that retains the antibody specificity and immunoreactivity.

It is also specifically contemplated within the scope of the invention that the anti-cytokine or anti-inflammatory agent pharmaceutical compositions comprising HR341g, aminopterin, methotrexate or a functional derivative thereof may be "concurrently" administered to a patient. Concurrently administering means the anti-cytokine or anti-inflammatory agents are administered to the subject either (a) simultaneously in time (optionally by formulating the two together in a common carrier), or (b) at different times during the course of a common treatment schedule. In the latter case, the anti-cytokine or anti-inflammatory agent compounds are administered sufficiently close in time to achieve the intended effect. The active agents may be administered together in a single pharmaceutical composition or separately. The active agents of HR341g (i.e., the anti-cytokine or anti-inflammatory agents comprising sodium monofluorophosphate and/or aminopterin, methotrexate or a functional derivative thereof, as well as the other components of HR341g) should be present in the patient at sufficient combined levels to be therapeutically effective. The routes of administration of the anti-cytokine or anti-inflammatory agents comprising HR341g.(e.g., sodium monofluorophosphate, and/or aminopterin, methotrexate or a functional derivative thereof) may be the same or different. For any route of administration, single or divided doses may be used.

In one embodiment, the pharmaceutical composition used for the methods of the present invention comprises an HR341g-based composition comprised of the following ingredients in the recited percentages: Dicalcium phosphate dihydrate (DCP) 21.4% (w/v), insoluble sodium metaphosphate 13% (w/v); sorbitol syrup (70% solution) 23.3% (w/v) guar gum 4.2% (w/v); xanthan gum 1.7% (w/v); monosodium phosphate 0.28% (w/v); sodium monofluorophosphate 8.9% (w/v); aminopterin 0.0015% (w/v); titanium dioxide 0.56%

(w/v); sodium dodecylbenzene sulphate 0.46% (w/v); water 22.4% (w/v); trimagnesium phosphate 0.74% (w/v); and hydroxethyl cellulose ester 2.9% (w/v). Example 1 outlines the procedure for preparing one of the pharmaceutical compositions of the invention.

In another embodiment, the pharmaceutical composition used for the methods of the present invention comprises an HR341g-based composition comprised of the following ingredients in the recited percentages: Dicalcium phosphate dihydrate (DCP) 21.4% (w/v), insoluble sodium metaphosphate 13% (w/v); sorbitol syrup (70% solution) 23.3% (w/v) guar gum 4.2% (w/v); xanthan gum 1.7% (w/v); monosodium phosphate 0.28% (w/v); sodium monofluorophosphate 8.9% (w/v); titanium dioxide 0.56% (w/v); sodium dodecylbenzene sulphate 0.46% (w/v); water 22.4% (w/v); trimagnesium phosphate 0.74% (w/v); and hydroxethyl cellulose ester 2.9% (w/v).

While not intended to be limited by any particular mechanism of action, the brief description provided herein below provides one possible mechanism of action for the compositions of the present invention. Thus, by way of illustration only, and not by way of limitation, FIGS. 1A-1I illustrates in diagramatic form the formation of edema following a burn injury, and the effect of administration of HR341g on inflammatory cytokines such as tumor necrosis factor alpha (TNFa), IL-1, IL-6, and IL-8, and other inflammatory molecules such as NO and ROI.

In particular, with respect to FIG. 1, FIG. 1A illustrates intact skin and the underlying blood vessels. White blood cells are circulating in the blood at a concentration of about 4 million cells per milliliter of blood. FIG. 1B illustrates that the acute burn injury causes immediate mechanical destruction of skin cells, generating an ulceration. FIG. 1C illustrates that the acute burn injury generates immediate inflammation which results in production of the inflammatory cytokines tumor necrosis factor alpha (TNFa), IL-1, IL-6, and IL-8. These cytokines originate from cells in the skin and cells in the deeper tissues. FIG. 1D illustrates that under the influence of IL-8 (a white blood cell attractant), white blood cells in the blood vessels are called into the tissues. The white blood cells dissolve small portions of the blood vessel walls in order to leave the blood circulation and infiltrate the tissues to arrive at the burn site. The white cells attempt to repair the damaged tissues and fight infection. FIG. 1E illustrates that under the influence of TNFa and IL-1, the cells that line the blood vessels lose their integrity, and this results in pore formation along the blood vessels. This results in leakage of plasma from the blood vessels that causes edema fluid to form in the surrounding tissues. FIG. 1F illustrates that TNFa, IL-1, IL-6, and IL-8 are joined by other inflammatory substances, such as nitric oxide (NO) and free radicals (also called reactive oxygen intermediates or ROI). One important effect of these substances is dilation of the blood vessels that causes low blood pressure, and this results in reduced blood pressure and even shock. FIG. 1G illustrates that TNFa, IL-1, IL-6, and IL-8 and the other inflammatory substances, such as NO or ROI gain access to the blood stream and cause systemic inflammation. FIG. 1H illustrates that once TNFa, IL-1, IL-6, and IL-8 and the other inflammatory substances, such as NO or ROI enter the blood stream, they cause systemic inflammation. This can damage any organ system in the body, including organs such as heart kidneys, lungs and the brain. The systemic inflammation also causes fever. FIG. 1I illustrates that HR341g is believed to block production of TNFa, IL-1, IL-6, and IL-8 that initiate the inflammatory process. This not only reduces the local and systemic damage that these molecules can cause, but administration of HR341 g also blocks the formation of secondary inflammatory molecules such as nitric oxide or reactive oxygen intermediates.

The anti-inflammatory effects of HR341g will serve one or more of the following functions, either alone or any combination thereof: prevent the destruction of the epidermis and dermis by debridement and skin grafts; prevent hypertrophic scarring and other deformities-including loss of hair growth; stop the depletion of various metabolic fluids; act as a molecular antibiotic; act as a protease inhibitor; acts as a signal transduction inhibitor-blocks cell signaling channels between activated receptors on cells and intracellular components; prevent infections and return the dermis and epidermis back to the original form, texture, elasticity and strength; promote hair growth and hair restoration at the area of treatment; inhibits overexpression of enolase in a number of biochemical recognition processes. The chemoenzymatic approach appears vulnerable to exploitation by fluoride reagents (such as, but not limited to, sodium monofluorophosphate) as a substrate. (Harper's Biochemistry, 25th Edition, Eds. Murray et al. Chapter 19 (2000), incorporated by reference herein).

In particular, after triggering an inflammatory response as a result of a burn, burn patients have been found to have an increased susceptibility to subsequent inflammatory stimuli and infections. For example, if levels of lymphocyte and macrophage derived cytokines are examined, evidence shows that increased vascular permeability and inflammatory cytokine activation (interleukin-1, interleukin-6 and tumor necrosis factor-alpha) were induced in patients with burns. It was further found that patients were at increased risk for immunosuppression after a burn, which in turn increases the risk of infection.

The compositions and methods of the present invention prevent edema (in part) by blocking cytokine production by human peripheral mononuclear cells found in the blood and those produced by fibroblasts in the skin. In fact, burns induce tumor necrosis factor and interleukin-1, which in turn causes an increase in interferon-gamma (IFN-gamma) and lower levels of interleukin-12 (IL-12) expression. These pro-inflammatory cytokines cause capilliary leaks (increased permeability) which results in edema formation. This can be counteracted with the compositions of the present invention. For example, anti-cytokine or anti-inflammatory agents comprising aminopterin, methotrexate or a functional derivative thereof, including HR341g or a functional derivative thereof, will act as a cytokine inhibitor. For example, HR341g and derivatives thereof may reduce capillary membrane permeability by inhibiting cytokines and nitric oxide. Thus, the dehydration of the intra-vascular system is prevented and there is no overflow of plasma in the intercellular space, nor between the epidermal, dermal junction. Edema does not develop because the plasma remains in the intravascular system.

Methods of Use

Thus, in its simplest aspect, the present invention provides a method for treating all forms of burns comprising administering to a burn area of a subject in need thereof of a therapeutically effective amount of a composition comprising an anti-cytokine or anti-inflammatory agent or both, or a functional derivative thereof; and a pharmaceutically acceptable excipient.

In another aspect, the present invention relates to methods of controlling or alleviating pain by reducing the severity of edema associated with a burn comprising administering to a subject in need thereof a therapeutically effective amount of a pharmaceutical composition comprising an anti-cytokine or anti-inflammatory agent or both, or a functional derivative thereof; and a pharmaceutically acceptable excipient, wherein said pharmaceutical composition inhibits one or more components of the inflammatory pathway.

In another aspect, the present invention also relates to a method for promoting rapid regeneration of damaged tissues resulting from a burn comprising administering to a subject in need thereof a therapeutically effective amount of a pharmaceutical composition comprising an anti-cytokine or anti-inflammatory agent or both, or a functional derivative thereof; and a pharmaceutically acceptable excipient, wherein said pharmaceutical composition promotes rapid regeneration of damaged tissues while retaining the original composition of the tissue and minimizing the complications and scarring associated with a burn.

In certain embodiments of the invention, the burn being treated is a chemical, radiation, electrical, sunburn, heat, extreme cold- or thermally-induced burn, or any combination thereof.

Thus, in yet another aspect, the present invention also relates to a method for preventing or ameliorating the adverse affects associated with controlled thermal induced skin damage employed in scar and tattoo removal, cancer excisions, cautery excision of polyps, ulcers, treatment of decubitus ulcers (bedsores), and/or acne comprising administering to a subject in need thereof a therapeutically effective amount of a pharmaceutical composition comprising an anti-cytokine or anti-inflammatory agent or both or a functional derivative thereof; and a pharmaceutically acceptable excipient, wherein said pharmaceutical composition promotes rapid regeneration of damaged tissues while retaining the original composition of the tissue and minimizing the complications and scarring associated with the thermally induced burn in one or more of the recited conditions.

In yet another aspect of the invention, a method is provided for suppressing or modulating the immune system in a mammalian patient in need of such immunosuppression comprising administering to said patient an immunosuppressing effective amount of a therapeutically effective amount of a pharmaceutical composition comprising an anti-cytokine or anti-inflammatory agent or both or a functional derivative thereof; and a pharmaceutically acceptable excipient.

In yet another aspect of the invention, a method is provided for suppressing the synthesis of potentially harmful inflammatory molecules comprising cytokines, interleukins (for example, IL-1, IL-8, IL-12, IL-18, TNF), nitric oxide, reactive oxygen intermediates (ROI), prostaglandins, or any one or more of the known biological molecules involved in inflammatory signal transduction pathways, in a mammalian patient in need of such anti-inflammation comprising administering to said patient an antiinflammatory effective amount of a therapeutically effective amount of a pharmaceutical composition comprising HR341 g or a functional derivative thereof; and a pharmaceutically acceptable excipient, wherein said pharmaceutical composition suppresses the synthesis of interleukins (for example, IL-1, IL-2, IL-8, IL-12, IL-18, TNF), nitric oxide, reactive oxygen intermediates (ROI), prostaglandins, or any one or more of the known biological molecules involved in inflammatory signal transduction pathways.

As used herein, the term "cytokine" is a generic term for proteins released by one cell population which act on another cell as intercellular mediators. Examples of such cytokines are tumor necrosis factor-alpha and -beta; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-8, IL-12, or IL-18; and other polypeptide factors including leukemia inhibitory factor (LIF) and kit ligand (KL). As used herein, the term cytokine includes proteins from natural sources or from recombinant cell culture and biologically active equivalents of the native sequence cytokines.

In yet another aspect of the invention, a method is provided for modulating expression of major histocompatibility complex (MHC) molecules in a mammalian patient in need of such immunosuppression comprising administering to said patient an immunosuppressing effective amount of a therapeutically effective amount of a pharmaceutical composition comprising HR341 g or a functional derivative thereof; and a pharmaceutically acceptable excipient, wherein said pharmaceutical composition modulates expression of major histocompatibility complex molecules.

In yet another aspect of the invention, a method is provided for limiting intramolecular nucleophilic reactions that occur in most pathways that affects the reactivity of intramolecular and intermolecular groups comprising administering to a patient in need thereof a therapeutically effective amount of a pharmaceutical composition comprising an anti-cytokine or anti-inflammatory agent or a functional derivative thereof; and a pharmaceutically acceptable excipient. A number of oxygen groups or ROI are unstable in burn injuries and treatment with an anti-cytokine or anti-inflammatory agent such as HR341g will inhibit these oxygen free radicals or oxidants.

In another embodiment, the pharmaceutical compositions of the present invention are thus useful to treat the pain and tissue dysfunction associated with and/or prevent a diseases or disorders often accompanying a burn. Since HR341 g reduces inflammation, it may be used to treat diseases where inflammation is thought to cause pathology or tissue damage. A list of the typical ADRs includes, but is not limited to, those which are burn-associated such as compartment syndrome, acidosis, acute renal failure, acute tubular necrosis, cellulitis, secondary seizures, contractures, reduced end-organ perfusion, endotoxemia, exotoxemia, gangrene, nosocomial pneumonia (50% of patients with burn/smoke inhalation injury develop this type), ARDS (acute respiratory distress syndrome), ventilator associated pneumonia, sepsis, septic shock, thromboembolic complications, and those other non-burn associated diseases with an inflammatory component such as, but not limited to, anemia, cancer, congestive heart failure, reduced end-organ perfusion, dermatomyositis (DM), dermatitis, alveolar proteinosis pneumonia, bronchcolotis obliterans organizing pneumonia (BOOP), chronic aspiration lipoid pneumonia, community acquired pneumonia (CAP), coronavirus pneumonia, cryptoccal pneumonia, chlamydia pneumonia, desquamative interstitial pneumonia, eosinophilic pneumonia, *haemophilus influenza* pneumonia, *haemophilus influenza* pneumonia, *haemophilus parainfluenzae* pneumonia, idiopathic pneumonia, influenza associated pneumonia, idiopathic interstitial pneumonia, *kliebsiella* pneumonia, *mycoplasma* pneumonia, non-specific interstitial pneumonia (associated with dermatomyositis-DM), *pasteurella multocida* pneumonia, *pneumocystis carinnii*-(PCP) pneumonia, *pseudomonas aeruginosa* pneumonia, respiratory synctial virus infection, staphylococcal necrotising pneumonia, tuberculosis pneumonia, usual interstitial pneumonitis (UIP), varicella zoster virus pneumonia, toxic shock syndrome, and toxic epidermal necrosis (TEN). The following list of diseases are associated with metabolic disarray because of thermal injuries: cachexia, diarrhea, encephalopathy, myglobulinuria, and neurities.

The drugs and/or topical agents that are conventionally used to treat burns are limited in their use and scope. Table 1 indicates the drugs, listed with their benefits and drawbacks. None of these drugs, however, prevent or stop edema associated with burns, since they have not been demonstrated to block the inflammatory response. The present invention specifically provides for inclusion of one or more of the conventional drugs in combination with HR341g.

TABLE 1

| Drug | Type | Benefits | Drawbacks |
| --- | --- | --- | --- |
| Bacitracin | Ointment-Polypeptide Antibiotic | Effective against gram-positive cocci and bacilli. Inhibits cell wall synthesis of bacteria. Enchances re-epithelialization. Safe, non-toxic | Ineffective against gram-negative organisms, and fungi. Shown to have a negative effect on keratinocyte proliferation. Some incidences of resistant strains. Use a petrolatum base that increase maceration. Ineffective against thickness injuries. Must be used up to 3 times a day. |
| Polymyxin B Sulfate | Ointment-Simple, basic peptide anti-biotic | Effective agains gram-negative organisms. Contains surface bacteria. Affects cell membrane permeability, killing microorganisms. Non-toxic unless used for prolonged periods | Ineffective against gram-positive organisms. It is petrolatum based and therefore promotes maceration. Must be used up to 3 times a day. Caused massive reductions in keratinocyte proliferation. Is ineffective against gram-negative strains of *P. aeruginosa*. Suppresses PMN ability to destroy microorganisms. |
| Neomycin | Ointment-Broad spectrum anti-biotic also can be used. Can be used as a cream | Particularly effective against gram-negative organisms and the gram-positive strain of *S. aureus*. Controls the protein synthesis of bacteria by binding to a ribosomal subunit. Inhibits the proliferation of bacteria on wound surfaces. | Resistant organisms are common. Is ineffective against some gram-negative and some gram-positive organisms. Ointment form promotes maceration. Hypersensitivity occurs frequently (5% to 8%). Ototoxicity and Nephrotoxicity has been reported in cases with TBSA of 20% or more. |
| Polysporin/ Neosporin | Ointment-(Polysporin) is a combination of Polymyxin B Sulfate and Bacitracin. (Neosporin) is a combination of Neomysin, Polymyxin B Sulfate. | Effective against gram-positive cocci and bacilli. Effective against some gram-negative organisms. Contains surface bacteria. Inhibits the proliferation of bacteria on wound surfaces. | Cannot be used on burns of 20% or more of TBSA. Petrolatum base promotes maceration. Causes massive reductions in keratinocyte proliferation. Is ineffective against most strains of *P. aeruginosa*. Suppresses PMN ability to destroy microorganisms. Ineffective when used on full thickness injuries. |
| Povidone-Iodine | Ointment-Wide bactericidal spectrum | Effective against most strains of gram-positive and gram-negative organisms. Able to oxidize microbial protoplasm. Also effective against *candida* and most fungi. | Causes substantial delays in wound healing. Toxic to fibroblast cells and keratinocytes. PMN or Polymorphonuclear leukocytes are inhibited by exposure to this drug. Toxic to children and pregnant women. |
| Silver Sulfadiazine 1%-Cream | Cream-Topical Sulfonamide of Silver Nitrate and Sodium Sulfadiazine and prepared in a 1% water miscible | Particularly effective against a wide range of flora which include several strains of gram-negative bacteria and a few gram-positive oraganisms. Superinfection and resistance is rare. Promotes wound healing because of its bactericidal properties. Easy to use. Causes no | Retardation of healing time likely to be expected because drug is toxic to keratinocytes and fibroblasts. Inhibits the effects of PMN in killing microorganisms. Also limits local lymphocyte function. The development of kernicterus puts pregnant |

TABLE 1-continued

| Drug | Type | Benefits | Drawbacks |
| --- | --- | --- | --- |
| | cream. | pain. Used for deep partial and full thickness wounds. | women and infants at extreme risks for damage. |
| Nitrofurazone 0.2% Compound | Cream-Broad anti bacterial spectrum | Effective against several gram-negative and a couple of gram-positive organisms. The mechanism of action appears to be by inhibition of bacterial enzymes. Causes no pain following application. Formation of resistant bacterial is rare. Can be mixed with other drugs | Development of contact dermatitis, rash, local edema, and pruitus has been reported. Not effective against any fungal organisms, or against gram-negative *P. aeruginosa*. Very toxic to fibroblasts. A detrimental effect on the growth and migration of keratinocytes. |
| Gentamicin 0.1% | Cream-Broad anti-bacterial spectrum | Effective against several gram-negative organisms. Inhibits protein synthesis and messenger ribonucleic acid translation. Not excessively toxic to keratinocytes. Easy to apply. No pain is associated with its application. | Not effective against most gram-positive and some gram-negative organisms. Resistant organisms are common with its use. Hypersensitivity is common also. Ototoxicity and nephrotoxicity sometimes occur, especially when the drug is used in large volumes over an extended period of time. |
| Manfenide Acetate 0.5% Cream (Sulfamylon) | Cream-Methylated Sulfonamide Compound | Wide range of antibacterial activity against most gram-positive and gram-negative pathogens. The formation of resistant organisms is rare. Controls superficial infections. Readily absorbed into eschar and therefore high effective against invasive wound infection. | The risk of toxcity is high with risk to respiratory status and ph status. Cases of super infection with *candida* can develop occassionally. Rashes occur in 50% of the patients treated. Toxicity increases in correlation to the TBSA burned and treated. Is toxic to both keratinocytes and fibroblasts. |
| Nystatin | Cream-Fungicide | Effective against the most common *candida* fungal infection. Aid healing by containing contagions. Hypersentivity reactions are rare, even with extended use. Not toxic to keratinocytes or fibroblasts. Increased cell wall permeability is the mechanism for the drugs fungicidal action. | Several strains of *candida* can develop resistance. It is not effective against either gram-positive or gram-negative microorganisms. Must be applied 3 times a day. Not effective when combined with other agents. Limited in its use, and is prone to super infection outbreaks in burn units. |
| Acetic Acid 0.5% | Solution-Acid based anti-bacterial agent | Effective against many gram-positive and gram-negative microorganisms, especially *P. aeruginosa*. Penetrates cell wall and disrupts the cell membrane. | Reduced epithelial cell proliferation. Very toxic to regenerating epithelium. Reduces PMN function. Skin irritation is common. Acidosis results from protracted use over large surface area wounds. Toxic to fibroblasts. Must be applied frequently to keep the wound moist. Must wash the wound between aplications. |
| Sodium Hypochlorite (Dakin's Solution) | Solution-General bactericidal, fungicidal, and virucidal agent | Effective against most gram-positive and some gram-negative microorganisms. Also effective against most fungal infections. Toxicity is rare. Effective against some viral infections. Used to irrigate wounds. | Toxic to fibroblast cells, keratinocytes, and inhibits the viability of of polymorphonuclear leukocytess. The drug dissolves blood clots and delays clotting. Bleeding is common in over 70% of th patients that are treated. |

TABLE 1-continued

| Drug | Type | Benefits | Drawbacks |
|---|---|---|---|
| Silver Nitrate 0.5% | Solution-General bactericidal agent. Wet to moist dressing | Most effective against gram-positive bacteria. Is invulnerable to resistant organisms. No cases of hypersensitivity reactions have occurred. The wound healing is enhanced by the control of local infection. Mildly effective against some gram-negative organisms. | Acidosis is common when TBSA is over 20% Extremely hypotonic because electrolytes leach into dressing, leading to chemical and electrolyte imbalance. Must be used on smaller TBSA burns because of toxicity. The application calls for frequent soaking every 2 hours. The solution is painful to apply. Patient must be monitered for blood methemoglobinemia. |
| TAB Solution (Triple Anti-biotic Solution) | Solution-Triple antibiotic. Wet to moist dressing. Also in an ointment. | Low level of tissue toxicity. A moderate level of activity against of a variety of gram-negative and gram-positive organisms. No resistant organisms are known to exist. Limited level of toxicity to keratinocytes. Uses Bacitracin, Polymyxin B and Neomycin | Gram-positive organisms such as P. aeruginosa are not effected by this drug. Occurences of hypersensitivity reactions have been recorded. Inhibits the ability of PMN's to destroy ingested microorganisms. Skin rashes occur often up to 10% of the patients studied. Ototoxity and nephrotoxicity have been reported. |
| Chlorhexi-Dine Solution | Solution-General Antibiotic | Effective against some gram-positive microorganisms. Apparently shows low levels of toxicity to cells and there are no data on tissue toxicity. Can be used for different depths and sizes of burns. | Ineffective against several varieties of both gram-negative and gram-positive organisms. Has no effect on fungal infections. Causes skin reactions with prolonged use, including contact dermatitis and skin rashes. Must be changed constantly. |

In each of the aforementioned aspects and embodiments of the invention, combination therapies other than those listed above in Table 1 are also specifically contemplated herein. In particular, the compositions of the present invention may be administered with one or more macrolide or non-macrolide antibiotics, anti-bacterial agents, anti-fungal agents, anti-viral agents, anti-parasitic agents, and/or anti-inflammatory or immunomodulatory drugs or agents.

Examples of macrolide antibiotics that may be used in combination with the composition of the present invention include, inter alia, the following synthetic, semi-synthetic or naturally occurring microlidic antibiotic compounds: methymycin, neomethymycin, YC-17, litorin, erythromycin A to F, oleandomycin, roxithromycin, dirithromycin, flurithromycin, clarithromycin, davercin, azithromycin, josamycin, kitasamycin, spiramycin, midecamycin, rokitamycin, miokamycin, lankacidin, and the derivatives of these compounds. Thus, erythromycin and compounds derived from erythromycin belong to the general class of antibiotics known as "macrolides." Examples of preferred erythromycin and erythromycin-like compounds include: erythromycin, clarithromycin, azithromycin, and troleandomycin.

Additional antibiotics, other than the macrolidic antibiotics described above, which are suitable for use in the methods of the present invention include, for example, any molecule that tends to prevent, inhibit or destroy life and as such, and as used herein, includes anti-bacterial agents, anti-fungal agents, anti-viral agents, and anti-parasitic agents. These agents may be isolated from an organism that produces the agent or procured from a commercial source (e.g., pharmaceutical company, such as Eli Lilly, Indianapolis, Ind.; Sigma, St. Louis, Mo.).

Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, oxazalidiinones, streptogramins, and fluoroquinolones. Examples of antibiotic agents include, but are not limited to, linezolid (Zyvax), dalfopristine, quinupristine, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefinetazole (CAS Registry No.: 56796-20-4); Cefotetan (CAS Registry No.: 69712-56-7); Cefprozil (CAS Registry No.: 92665-29-7); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

Anti-fungal agents include, but are not limited to, terbinafine hydrochloride, nystatin, amphotericin B, griseofulvin, ketoconazole, miconazole nitrate, flucytosine, fluconazole, itraconazole, clotrimazole, benzoic acid, salicylic acid, voriconazole, caspofungin, and selenium sulfide.

Anti-viral agents include, but are not limited to, amantadine hydrochloride, rimantadin, acyclovir, famciclovir, foscarnet, ganciclovir sodium, idoxuridine, ribavirin, sorivudine, trifluridine, valacyclovir, vangancyclovir, pencyclovir, vidarabin, didanosine, stavudine, zalcitabine, zidovudine, interferon alpha, and edoxudine.

Anti-parasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

In another aspect, in the method of the present invention, one may, for example, supplement the composition by administration of a therapeutically effective amount of one or more an anti-inflammatory or immunomodulatory drugs or agents. By "immunomodulatory drugs or agents", it is meant, e.g., agents which act on the immune system, directly or indirectly, e.g., by stimulating or suppressing a cellular activity of a cell in the immune system, e.g., T-cells, B-cells, macrophages, or other antigen presenting cells (APC), or by acting upon components outside the immune system which, in turn, stimulate, suppress, or modulate the immune system, e.g., hormones, receptor agonists or antagonists, and neurotransmitters; immunomodulators can be, e.g., immunosuppressants or immunostimulants. By "anti-inflammatory drugs", it is meant, e.g., agents which treat inflammatory responses, i.e., a tissue reaction to injury, e.g., agents which treat the immune, vascular, or lymphatic systems.

Anti-inflammatory or immunomodulatory drugs or agents suitable for use in this invention include, but are not limited to, interferon derivatives, e.g., betaseron, beta.-interferon; prostane derivatives, e.g., compounds disclosed in PCT/DE93/0013, e.g., iloprost, cicaprost; glucocorticoid, e.g., cortisol, prednisolone, methylprednisolone, dexamethasone; immunsuppressives, e.g., cyclosporine A, FK-506, methoxsalene, thalidomide, sulfasalazine, azathioprine, methotrexate; lipoxygenase inhibitors, e.g., zileutone, MK-886, WY-50295, SC-45662, SC-41661A, BI-L-357; leukotriene antagonists, e.g., compounds disclosed in DE 40091171 German patent application P 42 42 390.2; WO 9201675; SC-41930; SC-50605; SC-51146; LY 255283 (D. K. Herron et al., FASEB J. 2: Abstr. 4729, 1988); LY 223982 (D. M. Gapinski et al. J. Med. Chem. 33: 2798-2813, 1990); U-75302 and analogs, e.g., described by J. Morris et al., Tetrahedron Lett. 29: 143-146, 1988, C. E. Burgos et al., Tetrahedron Lett. 30: 5081-5084, 1989; B. M. Taylor et al., Prostaglandins 42: 211-224, 1991; compounds disclosed in U.S. Pat. No. 5,019,573; ONO-LB-457 and analogs, e.g., described by K. Kishikawa et al., Adv. Prostagl. Thombox. Leukotriene Res. 21: 407-410, 1990; M. Konno et al., Adv. Prostagl. Thrombox. Leukotriene Res. 21: 411-414, 1990; WF-11605 and analogs, e.g., disclosed in U.S. Pat. No. 4,963,583; compounds disclosed in WO 9118601, WO 9118879; WO 9118880, WO 9118883, antiinflammatory substances, e.g., NPC 16570, NPC 17923 described by L. Noronha-Blab. et al., Gastroenterology 102 (Suppl.): A 672, 1992; NPC 15669 and analogs described by R. M. Burch et al., Proc. Nat. Acad. Sci. USA 88: 355-359, 1991; S. Pou et al., Biochem. Pharmacol. 45: 2123-2127, 1993; peptide derivatives, e.g., ACTH and analogs; IL-1 receptor antagonists, IL-18 binding protein, activated protein C (Xigris), soluble TNF-receptors; TNF-antibodies; soluble receptors of interleukins, other cytokines, T-cell-proteins; antibodies against receptors of interleukins, other cytokines, and T-cell-proteins (the text of each of the afore-mentioned references is expressly incorporated by reference herein).

Additional Uses

The present invention also has applications in emergency kits outfitted to contain a pharmaceutical composition comprising an anti-cytokine or anti-inflammatory agent or a functional derivative thereof, including HR341g or a functional derivative thereof so that pharmaceutical formulations comprising an anti-cytokine or anti-inflammatory agent or a functional derivative thereof such as HR341g can be made available for use in every emergency first aid kit. Such topical formulations can be applied to the skin immediately or shortly after an accident or injury. For example, such emergency kits would be invaluable in each household for use in emergency household accidents, in the car, including residential vehicles, commercial vehicles, and most emergency response and police vehicles.

The present invention also has applications in all types of sunburn and would be employed in post-sun exposure care to prevent skin cancer, prevent blistering, sooth, cool and reduce/eliminate the pain of sunburns. The present invention also has applications in artificial suntanning salons.

The present invention also has applications in all fields of professional uses including for example, hospitals, emergency and burn treatment, doctor office, general practitioner's office, ambulances and emergency vehicles, high risk industries, fire fighting, military, navy, law enforcement, mechanical work shops, auto repair, welding etc., and restaurants.

The present invention also has applications in the field of fire extinguishers and fire retardant materials in general, as well as possible uses in mandatory safety equipment that are modified to contain HR341g.

The present invention additionally has applications in the field of cosmetics, including for example, sunburn care, burn treatment, treatment of certain cancers, scar removal, post laser treatment care, including, for example, lasers used in hair removal and other cosmetic procedures, as well as wrinkle removal.

Modes of Administration and Pharmaceutical Compositions

In general, the composition of the present invention is intended to be applied topically and directly to the burns or wound as described above. When the wound is deep, or the burn severe, it is preferred that the composition is in the form of an ointment, salve or cream which is spread directly onto the wound and then covered with a standard sterile dressing pad or other appropriate dressing material. Alternatively, the ointment, cream or salve of the present composition is applied directly onto the dressing pad or other appropriate dressing material. The pad or dressing material is then placed over the wound or burn with the medicine-side down. This latter approach works better when applying dressing to severe burns and shallow wounds. For first degree burns and slight abrasions, in addition, the composition may be applied in aerosolized form.

Thus, the pharmaceutical composition of the present invention is applied to a wound so as to cover the injured surface completely, e.g., with, for example, and not by way of limitation, one-quarter inch thickness of the pharmaceutical composition. The only limitation on the application is that the pharmaceutical composition should be applied within the first twenty minutes following the burn or injury but may also be applied as soon as possible but preferably before 12 hours. Dressing-change schedules are of course dictated by the condition of the wound. In highly-contaminated (wounds exhibiting significant amounts of pus) or weeping wounds or severe burns, dressing changes may be performed every four to six hours; in other wounds or burns, changes are performed less frequently, sometimes only one or two times per day.

Dressings are advantageously changed three to four times a day. Repeated daily dressing changes are continued until the wound or burn is healed. Healing time varies, depending upon the type and depth of the wound or the severity of the burn.

The present pharmaceutical composition is effective in the treatment of a large variety of wounds and burns to a mammal, subject or patient in need thereof where bacterial and fungal contamination would ordinarily occur in the absence of treatment. The present medicinal composition can of course also be used to treat burns and wounds in other mammals, such as veterinary animals including, without limitation, dogs, cats, other household pets, horses, farm animals, and the like.

The compounds of the present invention include pharmaceutically acceptable salts that can be prepared by those of skill in the art. As used herein, by "pharmaceutically acceptable salt" it is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in J. Pharmaceutical Sciences, 1977, 66: 1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzene-sulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary as ammonium, and mine cations, including, but not limited to ammonium, tetramethylammonium, tetraethylammonium, methylamine, dimethylamine, trimethylamine, triethylamine, ethylamine, and the like.

The present invention also provides pharmaceutical compositions which comprise one or more of the anti-cytokine or anti-inflammatory agent compounds described above formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracistemally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrathecally, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions, or emulsions as well as sterile powders for reconstitution into sterile injectable solutions or dispersions just prior to use. Examples of suitable aqueous and nonaqueous carders, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like.

Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drag in liposomes or microemulsions which are compatible with body tissues.

The injectable formulations can be sterilized, for example, by filtration through a bacteria-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol, or a suppository wax which are solid at room temperature but liquid at body temperature and therefore melt in the rectum or vaginal cavity and release the active compound.

The pharmaceutical compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a pharmaceutical composition of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a pharmaceutical compositions of this invention include powders, sprays, ointments, and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend as upon the activity of the particular pharmaceutical compound or analogue thereof of the present invention, the route of administration, the severity of the condition being treated, and the condition and prior medical history of the patient being treated. However, it is within the skill of the art to start doses of the pharmaceutical compound at levels lower than required to achieve the desired therapeutic effect and to gradually increase the dosage until the desired effect is achieved.

The pharmaceutical compositions of the present invention can be used in both veterinary medicine and human therapy. The magnitude of a prophylactic or therapeutic dose of the pharmaceutical composition of the invention in the acute or chronic management of pathology and pain associated with above-mentioned diseases or indications will vary with the severity of the condition to be treated and the route of administration. The dose, and perhaps the dose frequency, will also vary according to the age, body weight, and response of the individual patient. In general, the total dose range of the pharmaceutical composition of this invention is generally between about 0.001 to about 100 mg, preferably about 0.01 to about 20 mg, and more preferably about 16 mg of active compound per kilogram of body weight are administered topically to a mammalian patient. If desired, the effective dose may be divided into multiple doses for purposes of administration, e.g. two to four separate doses.

Alternatively, the total dose range of the active ingredients of this invention is generally between about 1 and 500 mg per 70 kg of body weight per day, or about 10 and 500 mg per 70 kg of body weight per day, between about 50 and 250 mg per 70 kg of body weight per day, and more preferably between about 100 and 150 mg per 70 kg of body weight per day.

It is intended herein that by recitation of such specified ranges, the ranges cited also include all those dose range amounts between the recited range. For example, in the range about 1 and 500, it is intended to encompass 2 to 499, 3-498, etc, without actually reciting each specific range. The actual preferred amounts of the active ingredient will vary with each case, according to the species of mammal, the nature and severity of the particular affliction being treated, and the method of administration.

It is also understood that doses within those ranges, but not explicitly stated, such as 30 mg, 50 mg, 75 mg, etc. are encompassed by the stated ranges, as are amounts slightly outside the stated range limits.

Alternatively, the total dose range of the pharmaceutical compositions of this invention is generally between about $10^{-8}$ and $10^{-3}$ molar range per 70 kg of body weight, or about $10^{-7}$ and $10^{-4}$ molar range per 70 kg of body weight, preferably between about $10^{-6}$ and $10^{-2}$ molar range per 70 kg of body weight, and more preferably between about $10^{-4}$ molar range per 70 kg of body weight (in cream form, aminopterin may be included up to 100 micromolar). It is intended herein that by recitation of such specified ranges, the ranges cited also include all those concentration amounts between the recited range. For example, in the range about $10^{-8}$ and $10^{-3}$ molar range, it is intended to encompass $1.1 \times 10^{-8}$ to $9.9 \times 10^{-4}$, $1.2 \times 10^{-8}$ to $9.8 \times 10^{-4}$, etc, without actually reciting each specific range. The actual preferred amounts of the active ingredients will vary with each case, according to the species of mammal, the nature and severity of the particular affliction being treated, and the method of administration. In any event, the concentration of the active ingredients in the topical cream formulation should include aminopterin or a functional derivative thereof in a concentration of 1-100 µM and/or sodium monoflourophosphate of 0.1 to 1.0 M. Particularly preferred concentrations for aminopterin or a functional derivative thereof are at a concentration of 33.13 µM (0.0015%) and/or sodium monoflourophosphate at a concentration of 0.663 M (8.9%).

In general, the pharmaceutical compositions of the present invention are periodically administered to an individual patient as necessary to improve symptoms of the particular disease being treated. The length of time during which the compositions are administered and the total dosage will necessarily vary with each case, according to the nature and severity of the particular affliction being treated and the physical condition of the subject or patient receiving such treatment.

It is further recommended that children, patients of age over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know, with no more than routine experimentation, how and when to interrupt, adjust, or terminate therapy in conjunction with individual patient response.

The term "unit dose" is meant to describe a single dose, although a unit dose may be divided, if desired. Although any suitable route of administration may be employed for providing the patient with an effective dosage of the composition according to the methods of the present invention, topical administration is preferred. Suitable routes include, for example, topical, transdermal, subcutaneous, intramuscular, by inhalation, and like forms of administration may be employed. Suitable dosage forms include nasal sprays, troches, dispersions, suspensions, solutions, patches, and the like, although topical and/or nasal dosage forms are preferred.

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention is illustrated by the Examples that follow, it being understood, however, that the invention is not limited to the specific details of these Examples.

EXAMPLE ONE

Introduction

This example outlines the procedure for preparing the pharmaceutical composition of the present invention.

Materials and Methods

Preparation of HR341g

HR341g is made according to the following procedure for the topical formulation. In brief, Dicalcium phosphate dihydrate (DCP), Insoluble sodium metaphosphate, Sorbitol syrup (70% solution), Guar gum, Xanthan gum or Pluronic-F87, Monosodium phosphate, Sodium monofluorophosphate, Aminopterin, Titanium dioxide, Sodium dodecylbenzene sulphate, Water, Trimagnesium phosphate, and Hydroxethyl cellulose ester are added to a high sheer mixer in the amounts shown in Table 2 (w/v), and filtered through a 0.007 inch screen.

TABLE 2

| Ingredients | Weight (w/v) | |
|---|---|---|
| Dicalcium phosphate dihydrate (DCP) | 1150 | grams |
| Insoluble sodium metaphosphate | 700 | grams |
| Sorbitol syrup (70% solution) | 1250 | grams |
| Guar gum | 225 | grams |
| Xanthan gum | 90 | grams |
| Monosodium phosphate | 15 | grams |
| Sodium monofluorophosphate | 477 | grams |
| Aminopterin | 80 | milligrams |
| Titanium dioxide | 30 | grams |
| Sodium dodecylbenzene sulphate | 25 | grams |
| Water | 1200 | grams |
| Trimagnesium phosphate | 40 | grams |
| Hydroxethyl cellulose ester | 157.5 | grams |

This formulation can be made in an approximately 5 kilogram quantity in a Molteni TM5 mixer or any other high shear mixer known to those of skill in the art, in the following stages. Mixing should be carried out under vacuum.

In stage 1, the ingredients are added in the following order and amounts: 90 degree Centigrade Water (1105 g) and Sorbitol Syrup (417 g) are put in the mixer. Monosodium Phosphate (15 g), Sodium Monofluorophosphate (477 g) and Aminopterin (80 mg) are then added and mixed for 12 minutes at 6,000 rpm. In stage 2, dry mix Guar Gum (225 g), Xanthan Gum (90 g), Titanium Dioxide (30 g), Dicalcium Phosphate Dihydrate (DCP) (1150 g), Insoluble Sodium Metaphosphate (700 g), and Hydroxethyl cellulose ester (157.5g) in a container and then slowly add dry mix combination into the stage I mix. Mix for 10 minutes at 7,000 rpm. In stage 3, sorbitol Syrup (417 g) is added into the mixer and mixed for 5 minutes at 7,000 rpm. In stage 4, Sodium Dodecylbenzene Sulphate (25 g) and Sorbitol Syrup (417 g) are added to the remainder of the room temperature mix for 5 minutes at 7,000 rpm. Separately mix dodecyl benzene sulphate (25 g) and sorbitol syrup (416 g) and 95 g room temperature water. This wet mix is then added into the high sheer mixer and mixed for 15 minutes at 7,000 rpm. Pumping the mixture through a 0.007 inch screen enhances the smoothness of the cream. The mix should be smooth with no grainy texture. Viscosity should be consistent throughout. When complete, the mixture is then packed into tubes.

Results

The finish product should be in the proportions shown in Table 3.

TABLE 3

| Ingredients | Weight (w/v) | Percentage (w/v) |
| --- | --- | --- |
| Dicalcium phosphate dihydrate (DCP) | 1150 grams | 21.4 |
| Insoluble sodium metaphosphate | 700 grams | 13.0 |
| Sorbitol syrup (70% solution) | 1250 grams | 23.3 |
| Guar gum | 225 grams | 4.2 |
| Xanthan gum | 90 grams | 1.7 |
| Monosodium phosphate | 15 grams | 0.28 |
| Sodium monofluorophosphate | 477 grams | 8.9 |
| Aminopterin | 80 milligrams | 0.0015 |
| Titanium dioxide | 30 grams | 0.56 |
| Sodium dodecylbenzene sulphate | 25 grams | 0.46 |
| Water | 1200 grams | 22.4 |
| Trimagnesium phosphate | 40 grams | 0.74 |
| Hydroxethyl cellulose ester | 157.5 grams | 2.9 |

EXAMPLE TWO

Introduction

This example outlines the testing of the pharmaceutical composition in the methods of the present invention. The study of three hypothetical burn patients is presented. These studies are designed to represent typical patients. Patients A, B and C were admitted to the hospital at the same time, with total burn surface area (TBSA) burns of 30%. The patients' burns were in the upper chest area, and on their upper backs. Patient C, in addition had small burns on the side of his face.

Post-burn injury in these patients is due to inflammation with associated edema that peaks several days post burn. Also, without surgery, 48 hours after a burn, bacterial microorganisms may invade the burn wound. In some patients, there is an extreme systematic inflammatory response to the burn. In what is described as "after burn", the systematic inflammatory response progresses until an "associated disease response" is evident.

Material and Methods

Patient A

Patient A arrives at the hospital 15 minutes after he was burned. The patient is suffering from $2^{nd}$ and $3^{rd}$ degree burns, and fluid resuscitation based upon the Parkland formula is administered to the patient. Within 2 hours inflammation and edema develop. The burn results in the release of local mediators. These mediators cause even more inflammation and edema to develop, and complement activation is triggered that causes further systemic mediator production.

Among these mediators, arachidonic acid, cytokine production (including IL-1 and TNF), NO, reactive oxygen intermediates (ROI), are produced. This results in neutrophil sequestration and priming of both neutrophils and macrophages locally and systematically.

The progression of burn wound inflammation increases, including the generation of circulating immunosuppressive compounds. IL-6 is released, which initiates liver acute phase protein production. Hyper metabolism develops resulting in muscle catabolism. The patient loses weight if inflammation is prolonged. Since both the neutrophils and macrophages are primed, massive amounts of oxidants, arachidonic acid metabolites, cytokines and proteases can be produced. This action causes further local and systemic inflammation that induces tissue damage. The higher levels of mediators, particularly cytokines, increase the damage, leading to even more inflammation.

Patient B

Patient B arrives at the hospital 15 minutes after he was injured; the patient is suffering from $2^{nd}$ and $3^{rd}$ degree burns and fluids based upon the Parkland formula are administered. HR341g is applied to the burn areas. Edema is substantially reduced at the burn site. There is some inflammation, which is necessary for proper healing, but there are no excessive reactions as in Patient A. Even though mediators such as cytokines, oxidants and arachidonic acid are released, the absolute amounts are smaller than in Patient A, and edema remains at manageable levels. Cytokine production and growth factors affect "target cells" through receptors found on the target cells. Most individual receptors are highly specific and can only recognize one molecule. So in the case of a burn wound, several cells may react to a single growth factor, yet each cell may respond differently. The specific receptors for each growth factor ensure that the cellular response will also be unique. Interleukin I (IL-1) is produced by macrophages, monocytes, skin cells, and its release can cause fever. IL-2 further stimulates T-lymphocytes and activates natural killer (NK) cells. Other interleukins stimulate the proliferation of bone marrow cells, either broadly or very selectively. Patient B has an increased recruitment of cells into the wound, increased collagen formation and organization and wound strength. Furthermore, Patient B suffered minimum associated disease responses (ADRs), because microorganisms need the environment of a burn wound to proliferate, that environment has been altered with HR431 g.

Patient C

Patient C was intubated immediately because of facial burns. The risk is two fold because if the patient has pulmonary injury, then over 50% develop nosocomial pneumonia. There is also a 35% chance that if the patient is placed on a ventilator, he will also develop pneumonia. If pulmonary edema develops before the patient is placed on a ventilator, there is a near 100% chance that the patient will die. Patient C didn't suffer detectable pulmonary injury, but to be safe Patient C was placed on a ventilator.

Patient C develops thermal edema 2 hours after being admitted to the hospital. The results of inflammatory changes caused by the release of cytokines such as TNF, IL-1, IL-2, IL-8, and IL-6. These increases cause additional priming of neutrophils released from the bone marrow. IL-1 action causes T-cell proliferation by inducing more IL-2 receptors. Immediately, Patient C begins to show the effects of post-burn hemodynamic instability. The patient's blood pressure is altered, cardiac output falls, and signs of hypovolemia are revealed. However, intravascular volume is maintained and cardiac output returns to normal over the next 24 hours. A generalized capillary leak occurs in unburned areas. However, this capillary permeability is only transiently changed in the unburned areas. Vasoactive amine release is the cause of the increased microvascular permeability. The edema may be exacerbated due to burn induced hypoproteinemia.

In the next 48 hours the patient is infected by gram-positive microorganism and 72 hours after that, by gram-negative pathogens. Since the capillary leak that occurred immediately after the burn was never addressed. Patient C's burn was incompletely addressed. Patient C's circulating immunosuppressive compounds, such as adrenal corticosteroids, anti-inflammatory cytokines (for example, IL-10), vasodilator prostaglandins PGE, $PGE_2$ $PGl_2$, are increased drastically. Increased IL-1 and TNF, above certain levels, increases hypermetabolism and organ dysfunction. Patient C suffers from circulating endotoxin, even in the absence of a clinically salient septic focus. The mechanism of the endotoxemia is absorption from the bacteria-colonized burn wound, or from leaks in the gastrointestinal tract due to increased gut permeability. Endotoxin initiates the release of several mediators including arachidonic acid, metabolites, oxygen free radicals and cytokines. The increased permeability can amplify inflammation and induce a form of ischemia-reperfusion injury. Patient C also suffers from blood flow maldistribution and increased skeletal muscle catabolism. Anemia, and increasing liver acute phase protein production occurs.

Results

Patient A's condition deteriorates and hospital staff decide to perform surgery. It is estimated that it will take several operations to restore the patient's former quality of life.

Patient B recovers, because edema was controlled. The patient needs no surgery and is released in 3 months with a high quality of life.

Patient C never recovered from his injuries. The patient suffered several ADR's, debridments, escharotomies and skin grafts. The patient also suffered several deformities including contractures, hypertophic scarring, and several operations. Patient C will spend over 5 years in and out of hospitals, and require a doctor's care for the rest of his life.

No burn patients suffer the same inflammatory reactions. Inflammation that supercedes certain thresholds interfere with the healing process. These changes can induce capillary leaks that alter chemical balances. The key component of the equation is the elimination of inflammation an associated edema and irreversible ischemia. Once inflammatory edema is reduced, patients will have a decreased requirement for not need skin grafts, debridment, escharotomies or any other type of surgery. HR341g blocks inflammation and edema formation by preventing further damage from after burn. In hospitals today inflammation and edema management is a primary focus. HR341g in conjunction with other treatments such as nutritional support and oxygen therapy can help patients recover faster and more completely Various publications have been referred to throughout this application. The disclosures of these publications in their entireties are hereby incorporated by reference into this application to more fully describe the state of the art to which this invention pertains.

EQUIVALENTS

The above examples have been depicted solely for the purpose of exemplification and are not intended to restrict the scope or embodiments of the invention. Other embodiments not specifically described should be apparent to those of ordinary skill in the art. Such other embodiments are considered to fall, nevertheless, within the scope and spirit of the present invention. Thus, the invention is properly limited solely by the claims that follow.

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: The sequence was artificially synthesized.  The
      alpha carbon of the lysine residue is bound to the alpha carbon of
      methotrexate.
<220> FEATURE:
<221> NAME/KEY: Binding
<222> LOCATION: (1)..(1)

<400> SEQUENCE: 1

Lys Gly Gly Tyr
1

<210> SEQ ID NO 2
<211> LENGTH: 4
<212> TYPE: PRT
<213> ORGANISM: Artificial Sequence
<220> FEATURE:
<223> OTHER INFORMATION: The sequence was artificially synthesized.  The
```

```
        arginine residue is bound to the epsilon carbon of methotrexate.
<220> FEATURE:
<221> NAME/KEY: Binding
<222> LOCATION: (1)..(1)

<400> SEQUENCE: 2

Arg Gly Gly Tyr
1

<210> SEQ ID NO 3
<211> LENGTH: 4
<212> TYPE: PRT
<213> ORGANISM: Artificial Sequence
<220> FEATURE:
<223> OTHER INFORMATION: The sequence was artificially synthesized.  The
        arginine residue is bound to the epsilon carbon of aminopterin.
<220> FEATURE:
<221> NAME/KEY: Binding
<222> LOCATION: (1)..(1)

<400> SEQUENCE: 3

Arg Gly Gly Tyr
1
```

What is claimed is:

1. A method for reducing the severity of inflammation and edema associated with a burn injury, comprising administering a pharmaceutical composition to a mammal having a burn injury in need thereof, the pharmaceutical composition comprising:

a) a therapeutically effective amount of sodium monofluorophosphate;

b) a therapeutically effective amount of a dihydrofolate reductase inhibitor selected from the group consisting of aminopterin, methotrexate, pyramethamine, trimethoprim, a functional derivative of aminopterin, and a functional derivative of methotrexate, wherein the functional derivatives of aminopterin are selected from the group consisting of 3',5'-dichloroaminopterin; 5,8-dideaza 5,6,7,8-tetrahydroaminopterin; 5,8,10-trideazaminopterin; 5,10-dideazatetrahydrofolic acid; 8,10-dideazaminopterin; aminopterin-gamma-hydrazide; aminopterin-alpha-hydrazide; 3',5'-dichloraminopterin-gamma-hydrazide; 3',5'-dichloroaminopterin-alpha-hydrazide; aminopterin-gamma-tyrosyl-hydrazide; aminopterin alpha-alpha-lysyl-glycyl-tyrosyl-hydrazide; aminopterin-alpha-alpha-lysyl hydrazide; aminopterin-alpha-alpha-lysine; aminopterin-alpha-alpha-lysyl-epsilon-arginine-glycine-glycine-tyrosine (SEQ ID NO: 3); alpha-methyl, alpha-ethyl, alpha-propyl, alpha-butyl, alpha-pentyl, alpha-hexyl, alpha-heptyl, alpha-octyl, and alpha-benzyl carboxylesters of aminopterin; alpha-amide, alpha-butylamide, alpha-benzylamide, and alpha-amidoethane sulfonic acid carboxylamides of aminopterin; alpha-glycyl, alpha-aspartyl, alpha-glutamyl, and alpha-polyglutamyl carboxylpeptides of aminopterin; gamma-methylester, gamma-ethylester, gamma-propylester, gamma-butylester, gamma-pentylester, gamma-hexylester, gamma-heptylester, gamma-octylester, and gamma-benzylester alpha-carboxylhydrazide-gamma-carboxylesters of aminopterin; gamma-amide, gamma-butylamide, gamma-benzylamide, and gamma-amidoethane sulfonic acid carboxylamides of aminopterin; gamma-glycyl, gamma-aspartyl, gamma-glutamyl, and gamma-polyglutamyl carboxylpeptides of aminopterin; gamma-carboxylhydrazides of aminopterin; alpha-gamma-dimethylester, alpha-gamma-diethylester, alpha-gamma-dipropylester, alpha-gamma-dibutyl ester, alpha-gamma-dipentyl ester, alpha-gamma-dihexylester, alpha-gamma diheptylester, alpha-gamma-dioctylester, and alpha-gamma-dibenzylester dicarboxylesters of aminopterin; alpha-gamma-diamide, alpha-gamma-dibenzylamide, and alpha-gamma-diamidomethane sulfonic acid dicarboxylamides of aminopterin; alpha-gamma-diglycyl, alpha-gamma-diaspartyl, alpha-gamma-diglutamyl, and alpha-gamma-dipolyglutamyl dicarboxylpeptides of aminopterin; alpha-gamma-dicarboxylhydrazides of aminopterin; alpha-methylester-gamma-butylester, and alpha-methylester-gamma-benzylester dicarboxylesters of aminopterin; alpha-benzylester-gamma-butylamide, alpha-benzylester-gamma-benzylamide, alpha-benzylester-gamma-butylamide-p-toluene sulfonic acid, and alpha-benzylester-gamma-benzylamide-p-toluene sulfonic acid alpha-ester-gamma-amides of aminopterin; alpha-t-butylester-gamma-hydrazides of aminopterin; alpha-ester-gamma-peptides of aminopterin; alpha-amide-gamma-esters of aminopterin; alpha-amide-gamma-peptides of aminopterin; alpha-amide-gamma-hydrazides of aminopterin; alpha-peptide-gamma-esters of aminopterin; alpha-peptide-gamma-amides of aminopterin; alpha-peptide-gamma-hydrazides of aminopterin; alpha-hydrazide-gamma-amides of aminopterin; and alpha-hydrazide-gamma-peptides of aminopterin; and the functional derivatives of methotrexate are selected from the group consisting of 4-amino-4-deoxy-$N_{10}$-methylpteroyl-D,L-homocysteic acid (mAPA-D,L-HCysA); 4-amino-4-deoxy-$N_{10}$-methylpteroyl-L-cysteic acid (mAPA-L-CysA); 4-amino-4-deoxy-$N_{10}$-methylpteroyl-L-homocysteic acid (mAPA-L-HCysA); 4-amino-4-deoxypteroyl-D,L-homocysteic acid (APA-D,L-HCysA); 4-amino-4-deoxypteroyl-L-cysteic acid (APA-L-CysA); 4-amino-4-deoxypteroyl-L-homocysteic acid (APA-L-HCysA); 3',5'-dichloromethotrexate; 5,8-dideaza-5,6,7,8-tetrahydromethotrexate; methotrexate-gamma hydrazide; methotrexate-alpha-hydrazide; 3'5'-dichloromethotrexate-gamma-hydrazide; 3',5'-dichloromethotrexate-alpha-hydrazide; methotrexate-alpha-alpha-lysyl-glycyl-glycyl-tyrosyl hydrazide (SEQ ID NO: 1); methotrexate-gamma-tyrosyl hydrazide; methotrexate-alpha-alpha-lysyl hydrazide; methotrexate-alpha-alpha-lysine; methotrexate-alpha-alpha-lysyl-epsilon-arginine-glycine-glycine-tyrosine (SEQ ID NO: 2); 5,8-dideazamethotrexate; alpha-methyl, alpha-ethyl, alpha-propyl, alpha-butyl, alpha-pentyl, alpha-hexyl, alpha-heptyl, alpha-octyl, and alpha-benzyl carboxylesters of methotrexate; alpha-amide, alpha-butylamide, alpha-benzylamide, and alpha-amidoethane sulfonic acid carboxylamides of methotrexate; alpha-glycyl, alpha-aspartyl, alpha-glutamyl, and alpha-polyglutamyl carboxylpeptides of methotrexate; gamma-methylester, gamma-ethylester, gamma-propylester, gamma-butylester, gamma-pentylester, gamma-hexylester, gamma-heptylester, gamma-octylester, and gamma-benzylester alpha-carboxylhydrazide-gamma-carboxylesters of methotrexate; gamma-amide, gamma-butylamide, gamma-benzylamide, and gamma-amidoethane sulfonic acid carboxylamides of methotrexate; gamma-glycyl, gamma-aspartyl, gamma-glutamyl, and gamma-polyglutamyl carboxylpeptides of methotrexate; gamma-carboxylhydrazides of methotrexate; alpha-gamma-dimethylester, alpha-gamma-diethylester, alpha-gamma-dipropylester, alpha-gamma-dibutyl ester, alpha-gamma-dipentyl ester, alpha-gamma-dihexylester, alpha-gamma diheptylester, alpha-gamma-dioctylester, and alpha-gamma-dibenzylester dicarboxylesters of methotrexate; alpha-gamma-diamide, alpha-gamma-dibenzylamide, and alpha-gamma-diamidomethane sulfonic acid dicarboxylamides of methotrexate; alpha-gamma-diglycyl, alpha-gamma-diaspartyl, alpha-gamma-diglutamyl, and alpha-gamma-dipolyglutamyl dicarboxylpeptides of methotrexate; alpha-gamma-dicarboxylhydrazides of methotrexate; alpha-methylester-gamma-butylester, and alpha-methylester-gamma-benzylester dicarboxylesters of methotrexate; alpha-benzylester-gamma-butylamide, alpha-benzylester-gamma-benzylamide, alpha-benzylester-gamma-butylamide-p-toluene sulfonic acid, and alpha-benzylester-gamma-benzylamide-p-toluene sulfonic acid alpha-ester-gamma-amides of methotrexate; alpha-t-butylester-gamma-hydrazides of methotrexate; alpha-ester-gamma-peptides of methotrexate; alpha-amide-gamma-esters of methotrexate; alpha-amide-gamma-peptides of methotrexate; alpha-amide-gamma-hydrazides of methotrexate; alpha-peptide-gamma-esters of methotrexate; alpha-peptide-gamma-amides of methotrexate; alpha-peptide-gamma-hydrazides of methotrexate; alpha-hydrazide-gamma-amides of methotrexate; and alpha-hydrazide-gamma-peptides of methotrexate; and c) a pharmaceutically acceptable carrier.

2. The method of claim 1, wherein the dihydrofolate reductase inhibitor is aminopterin or methotrexate; and said pharmaceutical composition inhibits dihydrofolate reductase.

3. The method of claim 1, wherein the pharmaceutical composition further comprises a therapeutically effective amount of one or more anti-inflammatory compounds and/or a therapeutically effective amount of one or more immunomodulatory agents.

4. The method of claim 3, wherein the anti-inflammatory compound or immunomodulatory drug comprises at least one of interferon; betaseron or β-interferon; a prostane; iloprost or cicaprost; a glucocorticoid; an immunosuppressive; a lipoxygenase inhibitor; a leukotriene antagonist; ACTH; a soluble TNF-receptor; an anti-TNF-antibody; a soluble receptor of interleukin, a cytokine, an Il-1 receptor antagonist, or a T-cell-protein; an antibody against a receptor of interleukin, a cytokine, or a T-cell-protein; or a calcipotriol.

5. The method of claim 2, wherein the pharmaceutical composition further comprises a therapeutically effective amount of one or more additional anti-inflammatory compounds and/or a therapeutically effective amount of one or more additional immunomodulatory agents.

6. The method of claim 5, wherein the additional anti-inflammatory compound or additional immunomodulatory drug comprises at least one of interferon; betaseron or n-interferon; a prostane; iloprost or cicaprost; a glucocorticoid; an immunosuppressive; a lipoxygenase inhibitor; a leukotriene antagonist; ACTH; a soluble TNF-receptor; an anti-TNF-antibody; a soluble receptor of interleukin, an Il-1 receptor inhibitor, a cytokine, or a T-cell-protein; an antibody against a receptor of interleukin, or a T-cell-protein; or a calcipotriol.

7. The method according to claim 1, wherein the burn is either a first, second or third degree thermal burn, or a combination thereof.

8. The method according to claim 1, wherein the mammal is a human being.

9. The method according to claim 4, wherein the glucocorticoid is selected from the group consisting of cortisol, prednisolone, methyl-prednisolone, and dexamethasone.

10. The method according to claim 4, wherein the immunosuppressive is selected from the group consisting of cyclosporine A, methoxsalene, thalidomide, sulfasalazine, and azathioprine.

11. The method according to claim 4, wherein the lipoxygenase inhibitor comprises zileutone.

12. The method according to claim 6, wherein the glucocorticoid is selected from the group consisting of cortisol, prednisolone, methyl-prednisolone, or dexamethasone.

13. The method according to claim 6, wherein the immunosuppressive is selected from the group consisting of cyclosporine A, methoxsalene, thalidomide, sulfasalazine, and azathioprine.

14. The method according to claim 6, wherein the lipoxygenase inhibitor comprises zileutone.

15. The method according to claim 6, wherein the Il-1 receptor inhibitor comprises an IL-1 receptor antagonist.

16. The method according to claim 6, wherein the burn is either a first, second or third degree thermal burn, or a combination thereof.

17. The method according to claim 1, comprising administering the pharmaceutical composition topically.

18. The method according to claim 17, wherein the pharmaceutical composition comprises an ointment, salve or cream.

19. The method according to claim 17, comprising administering the pharmaceutical composition from 2 to 4 times.

20. The method according to claim 1, wherein the sodium monofluorophosphate is present in an amount of from 1.5% to 15% by weight per unit volume of the pharmaceutical composition.

21. The method according to claim 1, comprising administering the pharmaceutical composition within 12 hours of the burn injury.

22. The method according to claim 21, comprising administering the pharmaceutical composition within 20 minutes of the burn injury.

23. The method according to claim 1, wherein the therapeutically effective amount of the dihydrofolate reductase inhibitor is a dose of from 0.001 to 100 mg per 70 kg of body weight of said mammal.

24. The method according to claim 20, wherein the therapeutically effective amount of the dihydrofolate reductase inhibitor is a dose of from 0.01 to 20 mg per 70 kg of body weight of said mammal.

25. The method according to claim 1, comprising administering the pharmaceutical composition parenterally.

26. The method according to claim 25, wherein the pharmaceutical composition comprises a pharmaceutically acceptable solution, dispersion, suspension or emulsion.

27. The method according to claim 1, further comprising administering an antibacterial agent to said mammal.

28. The method according to claim 27, wherein the pharmaceutical composition comprises the antibacterial agent.

29. The method according to claim 1, wherein the administering the pharmaceutical composition comprises oral, systemic, implant, intravenous, topical, intrathecal, or nasal administration.

30. The method according to claim 1, wherein administering the pharmaceutical composition comprises spraying a burn victim with a fire extinguisher containing the pharmaceutical composition.

31. The method according to claim 1, wherein the pharmaceutically acceptable carrier comprises dicalcium phosphate dihydrate (DCP), insoluble sodium metaphosphate, sorbitol syrup solution, guar gum, xanthan gum, monosodium phosphate, titanium dioxide, sodium dodecylbenzene sulphate, water, trimagnesium phosphate, and hydroxethyl cellulose ester.

32. The method according to claim 1, wherein the pharmaceutical composition comprises about 21.4% dicalcium phosphate dihydrate (DCP) by weight, about 13% insoluble sodium metaphosphate by weight, about 23.3% sorbitol syrup solution by weight, about 4.2% guar gum by weight, about 1.7% xanthan gum by weight, about 0.28% monosodium phosphate by weight, about 0.56% titanium dioxide by weight, about 0.46% sodium dodecylbenzene sulphate by weight, about 22.4% water by weight, about 0.74% trimagnesium phosphate by weight, and about 2.9% hydroxethyl cellulose ester by weight.

33. The method according to claim 31, wherein the pharmaceutical composition comprises about 8.9% of sodium monofluorophosphate by weight, and about 0.0015% of the dihydrofolate reductase inhibitor by weight.

34. The method according to claim 1, wherein the pharmaceutical composition further comprises one or more macrolide antibiotics.

35. The method according to claim 1, wherein the pharmaceutical composition further comprises one or more non-macrolide antibacterial agents.

36. The method according to claim 1, wherein the pharmaceutical composition further comprises one or more anti-fungal agents.

37. The method according to claim 1, wherein the pharmaceutical composition further comprises one or more anti-viral agents.

38. The method according to claim 1, wherein the pharmaceutical composition further comprises one or more anti-parasitic agents.

39. The method according to claim 34, wherein the one or more macrolide antibiotics comprises at least one of methymycin, neomethymycin, litorin, erythromycin A to F, oleandomycin, roxithromycin, dirithromycin, flurithromycin, clarithromycin, davercin, azithromycin, josamycin, kitasamycin, spiramycin, midecamycin, rokitamycin, miokamycin, and lankacidin.

40. The method according to claim 35, wherein the one or more non-macrolide antibacterial agents comprises at least one of penicillins, cephalosporins, carbacephems, cephamycins, carbapenems, monobactams, aminoglycosides, glycopeptides, quinolones, tetracyclines, macrolides, oxazalidiinones, streptogramins, and fluoroquinolones.

41. The method according to claim 36, wherein the one or more anti-fungal agents comprises at least one of terbinafine hydrochloride, nystatin, amphotericin B, griseofulvin, ketoconazole, miconazole nitrate, flucytosine, fluconazole, itraconazole, clotrimazole, benzoic acid, salicylic acid, voriconazole, caspofungin, and selenium sulfide.

42. The method according to claim 37, wherein the one or more anti-viral agents comprises at least one of amantadine hydrochloride, rimantadin, acyclovir, famciclovir, foscarnet, ganciclovir sodium, idoxuridine, ribavirin, sorivudine, trifluridine, valacyclovir, vangancyclovir, pencyclovir, vidarabin, didanosine, stavudine, zalcitabine, zidovudine, interferon alpha, and edoxudine.

43. The method according to claim 38, wherein the one or more anti-parasitic agents comprises at least one of pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

* * * * *

UNITED STATES PATENT AND TRADEMARK OFFICE
CERTIFICATE OF CORRECTION

PATENT NO. : 7,604,797 B2 Page 1 of 1
APPLICATION NO. : 11/012210
DATED : October 20, 2009
INVENTOR(S) : Terry Lee Hicks It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 148 days.

Signed and Sealed this

Fifth Day of October, 2010

David J. Kappos
*Director of the United States Patent and Trademark Office*